United States Patent [19]

Hirai et al.

[11] Patent Number: 4,902,337
[45] Date of Patent: Feb. 20, 1990

[54] HERBICIDAL HYDANTOIN DERIVATIVES

[75] Inventors: Kenji Hirai; Takamasa Fuchikami; Atsuko Fujita, all of Kanagawa; Hiroaki Hirose; Masahiro Yokota, both of Chiba; Shoin Nagato, Tokyo, all of Japan

[73] Assignees: Sagami Chemical Research, Tokyo; Kaken Pharmaceutical Co., Ltd., Osaka; Chisso Corporation, Tokyo, all of Japan

[21] Appl. No.: 92,193

[22] Filed: Sep. 2, 1987

[30] Foreign Application Priority Data

Sep. 2, 1986 [JP] Japan ................... 61-205065
Sep. 2, 1986 [JP] Japan ................... 61-205066

[51] Int. Cl.$^4$ ............... A01N 43/50; C07D 233/96
[52] U.S. Cl. ............................. 71/92; 548/312; 548/314
[58] Field of Search ............. 548/314, 312; 71/92

[56] References Cited

U.S. PATENT DOCUMENTS 4,427,438  1/1984  Nagano et al. ............ 548/314 X

FOREIGN PATENT DOCUMENTS 0049841  4/1982  European Pat. Off. ............ 548/314
2102605  7/1971  Fed. Rep. of Germany ...... 548/314
2265742  10/1975 France ................................ 548/314
1550994  8/1979  United Kingdom ................ 548/314

OTHER PUBLICATIONS

Chemical Abstracts, 84:121824q(1976) [Japan Kokai 75, 117,773, Agawa et al., 9/16/75].

Primary Examiner—Richard A. Schwartz
Attorney, Agent, or Firm—Nixon & Vandehye

[57] ABSTRACT

Novel hydantoin derivative which is represented by the formula:

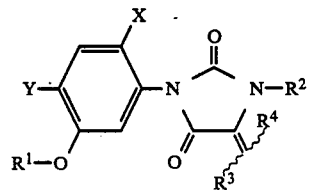

(wherein X and Y represent a halogen atom, $R^1$ represents a hydrogen atom, an alkyl group, a cycloalkyl group, an alkenyl group or an alkynyl group, $R^2$ represents a hydrogen atom, an alkyl group, an alkenyl group or an alkynyl group, and $R^3$ and $R^4$ independently represent a hydrogen atom or a lower alkyl group), and a herbicide containing said derivative as effective ingredient.

This hydantoin derivative exhibit excellent weed-killing activity for harmful weeds and low phytotoxicity for crop plants.

4 Claims, No Drawings

HERBICIDAL HYDANTOIN DERIVATIVES

This invention relates to novel hydantoin derivatives and herbicides containing the derivatives as an active ingredient and more particularly relates to hydantoin derivatives represented by the formula:

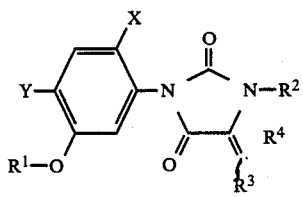

(wherein X and Y represent halogen atoms, $R^1$ represents a hydrogen atom, alkyl group, cycloalkyl group, alkenyl group, or alkynyl group, $R^2$ represents a hydrogen atom, alkyl group, alkenyl group or alkynyl group, $R^3$ and $R^4$ independently represent a hydrogen atom or lower alkyl group) and to herbicides containing the derivatives as an active ingredient.

It is known that some of hydantoin derivatives are compounds having a herbicidal activity or a fungicidal activity.

Hydantoin derivatives having a herbicidal activity are exemplified in Japanese patent publication Nos. 30695/1975 and 36332/1976, and Japanese Patent Laid-Open Nos. 58672/1982, 197268/1982, 219167/1983 and 69763/1986.

These hydantoin derivatives having a weed-killing activity, however, exhibit insufficient herbicidal activity against various weeds highly resistant to herbicides. A novel herbicidal compound having a high selectivity and a great weed-killing activity for such weeds in a small dosage have been desired.

The inventors of this invention have made certain studies and found that great weed-killing activities and a high selectivity for various weeds are imparted to herbecides by introducing various substituted phenyl groups at a nitrogen atom at the three-positions and alkyliden groups into the five-positions of hydantoin derivatives. These hydantoins are represented by the formula (1):

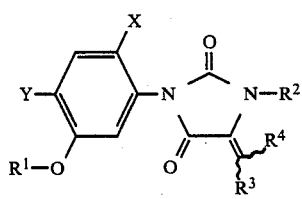

(wherein X, Y, $R^1$, $R^2$, $R^3$ and $R^4$ represent the substances defined above) does not injure cultivated plants such as rice, wheat, corn, cotton, beans, fruit trees, mulberry trees and lawn grass and so forth, while exhibiting superior herbicidal activity against weeds. Thus, the object of the present invention is to provide the hydantoin derivatives represented by the aforesaid formula (1) and herbicides containing the derivatives as an active ingredient.

One aspect of the present invention will now be described.

The novel hydantoin derivatives (to be described hereinafter as the subject compound according to the present invention) which is an effective ingredient of a herbicide is represented by the formula (1), wherein the halogen atom represented by X and Y is exemplified by fluorine, chlorine, bromine or iodine atom, preferably fluorine, chlorine or bromine. The alkyl group represented by $R^1$ is exemplified by a $C_1$ to $C_{12}$, preferably $C_1$ to $C_5$ straight or branched chain alkyl group, for example, methyl group, ethyl group, propyl group, isopropyl group, butyl group, isobutyl group, sec-butyl group, tert-butyl group, pentyl group, isopentyl group, neopentyl group, tert-pentyl group, hexyl group, isohexyl group, 1-methyl pentyl group, 2-methyl pentyl group, octyl group, 1-methyl octyl group, 2-ethyl hexyl group, decyl group or dodecyl group. The cycloalkyl group includes a $C_3$ to $C_{12}$ cycloalkyl group exemplified by cyclopropyl group, cyclopentyl group, cyclohexyl group or cyclododecyl group. The alkenyl group is a $C_2$ to $C_{10}$, preferably a $C_2$ to $C_6$ straight or branched chain alkenyl group which may be substituted by halogen, and is exemplified by allyl group, methallyl group, crotyl group, 1-methylallyl group, 1,1-dimethylallyl group, prenyl group, 3-methyl-3-butenyl group, 3-pentenyl group, 2-methyl-3-butenyl group, neryl group, geranyl group, 1-chloroallyl group, 2-chloroallyl group, 3-chloroallyl group, 3-bromoallyl group or 2-bromo-2-butenyl group. The alkynyl group is usually a $C_2$ to $C_5$ straight or branched chain alkynyl group, and is exemplified by propargyl group, 1-methyl propargyl group, 1,1-dimethyl propargyl group, 1-ethyl propargyl, 2-butynyl group, 1-methyl-2-butynyl group, 3-pentynyl group, 3-butynyl group, or 2-pentynyl group. $R^2$ is selected from the hydrogen, alkyl group, alkenyl group and alkynyl group defined by $R^1$. The lower alkyl group represented by $R^3$ and $R^4$ includes a $C_1$ to $C_4$ alkyl group, for example, methyl group, ethyl group, propyl group, isopropyl group, butyl group, sec-butyl group, or the like.

The typical examples of the novel hydantoin derivatives according to the present invention are summarized in the Table 1.

TABLE 1

Hydantoin Derivatives

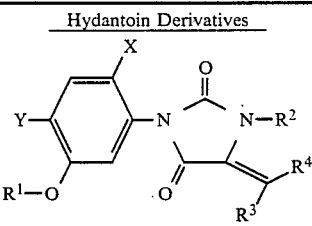

| Compound No. | X | Y | R$^1$ | Substituted Group R$^2$ | R$^3$ | R$^4$ |
|---|---|---|---|---|---|---|
| 1 | Cl | Cl | H | H | Me | Me |
| 2 | F | Cl | H | H | Me | Me |
| 3 | F | Br | H | H | Me | Me |
| 4 | F | Br | H | Me | Me | Me |
| 5 | Cl | Cl | i-Pr | H | Me | Me |
| 6 | F | Cl | HC≡CCH$_2$ | H | Me | Me |
| 7 | Cl | Cl | Me | Me | Me | Me |
| 8 | Cl | Cl | HC≡CCH$_2$ | Me | Me | Me |
| 9 | Cl | Cl | i-Pr | Me | Me | Me |
| 10 | F | Cl | Me | Me | Me | Me |
| 11 | F | Cl | i-Pr | Me | Me | Me |
| 12 | F | Cl | HC≡CCH$_2$ | Me | Me | Me |
| 13 | F | Cl | H$_2$C=C(Cl)CH$_2$ | Me | Me | Me |
| 14 | F | Cl | HC(Cl)=CHCH$_2$ | Me | Me | Me |
| 15 | F | Cl | HC≡CCH$_2$ | Et | Me | Me |
| 16 | F | Cl | HC≡CCH$_2$ | n-Hex | Me | Me |
| 17 | F | Br | Me | Me | Me | Me |
| 18 | F | Br | i-Pr | Me | Me | Me |
| 19 | F | Br | HC≡CCH$_2$ | Me | Me | Me |
| 20 | F | Cl | i-Pr | i-Pr | Me | Me |
| 21 | F | Cl | H$_2$C=CHCH$_2$ | Me | Me | Me |
| 22 | F | Cl | H$_2$C=C(CH$_3$)CH$_2$ | Me | Me | Me |
| 23 | F | Cl | cyclo-Pr | Me | Me | Me |
| 24 | F | Cl | cyclo-Pent | Me | Me | Me |
| 25 | Cl | Cl | cyclo-Hex | Me | Me | Me |
| 26 | Cl | Cl | HC(Cl)=CHCH$_2$ | HC(Cl)=CHCH$_2$ | Me | Me |
| 27 | Cl | Cl | i-Pr | HC≡CCH$_2$ | Me | Me |
| 28 | Cl | Cl | HC≡CCH$_2$ | HC≡CCH$_2$ | Me | Me |
| 29 | F | Cl | H$_2$C=C(CH$_3$)CH$_2$ | H$_2$C=C(CH$_3$)CH$_2$ | Me | Me |
| 30 | F | Br | i-Pr | HC≡CCH$_2$ | Me | Me |
| 31 | F | Br | H$_2$C=C(Cl)CH$_2$ | H$_2$C=C(Cl)CH$_2$ | Me | Me |
| 32 | F | Br | HC(Cl)=CHCH$_2$ | HC(Cl)=CHCH$_2$ | Me | Me |
| 33 | F | Br | HC≡CCH$_2$ | HC≡CCH$_2$ | Me | Me |
| 34 | F | Cl | Me | Me | Me | Et |
| 35 | F | Cl | H | H | Me | Et |
| 36 | F | Br | HC≡CCH$_2$ | H | H | i-Pr |

The herbicide according to the present invention containing the novel hydantoin derivative as an effective ingredient can exhibit a superior herbicidal activity against various weeds. Especially, it is capable of exhibiting a strong herbicidal effect against, for example, annual weeds such as Deccan grass (*Echinochloa Crusgalli*), *Monochoria vagiralis*, *Ammannia multiflora* and so forth, and perennial weeds growing mainly in paddy field such as nutsedge (*Cyperus microiria*), hardstembulrush (*Scirpus juncoides*), *Sagittaria pygmaea*, *Eleocharis acicularis*, Romer et Schultes and so forth. Further, this herbicide is capable of selectively killing upland weeds such as *Amaranthus lividus, Digitaria adscendens, Setaris viridis* P. Beauv., *Chenopodium album, Polygonum Longisetum, Amaranthus viridis, Portulaca oleracea, Plantago asiatica* and so forth.

Furthermore, since the compound according to the present invention has high herbicidal activity, the dosage of the compound employed for unit area can be kept small, as well as producing extremely small phytotoxicity for useful cultured platns. That is, the compound according to the present invention kills grassy weeds such as Deccan grass, crabgrass (*Digitaria abscendens*), *Setaria viridis* and so forth, but it does not shown any phytotoxicity with respect to the grassy crops such as rice, wheat and corns which are valuable crops. No phytotoxicity is also recognized for crops belonging to groups other than grasses such as soybeans, cotton, beans, fruit trees, mullberry trees and so forth, and lawn grass.

The compound according to the present invention is formulated into a desired form such as wettable powder, an emulsible concentrate, a dust formulation, granules and so forth, and so used as a herbicide in a conventional way by blending various carriers, extending agents, solvents, surface active agents, stabilizers and so forth.

In this formulation, other active ingredients, such as other types of herbicides, insecticides, fungicides, growth regulators and so forth, may be mixed in.

The dosage of the herbicide containing the compound according to the present invention depends on the manner of application, growth stage, type of plants to which it is applied, but is approximately 10 to 500 g per 10 acres, is preferably 30 to 300 g. The novel hydantoin derivative represented by the aforementioned formula (1) of the present invention can be prepared, for example, by the following method.

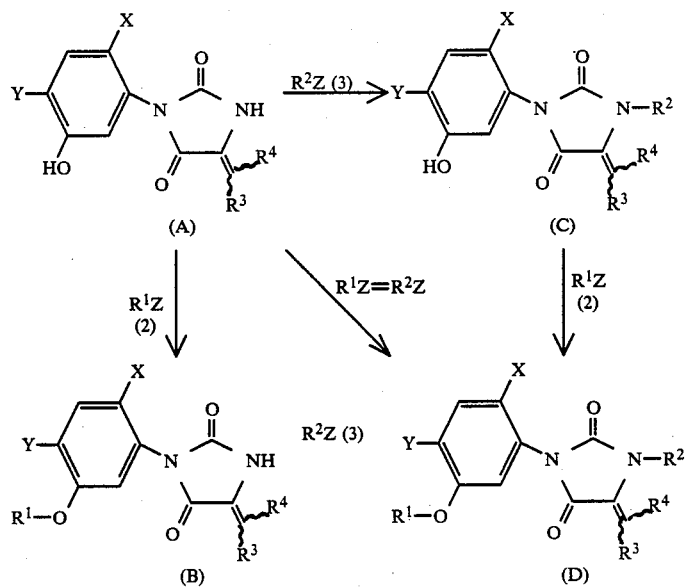

That is, in the reaction of the hydantoin derivative represented by the formula (A) [wherein, X, Y, $R^3$ and $R^4$ denote the same as those described above; these compounds are those of formula (1) in which $R^1$ and $R^2$ are respectively hydrogen atoms] with $R^1 Z$ or $R^2 Z$ represented by formulae (2) and (3) (wherein $R^1$ and $R^2$ denote the same as those mentioned above; and Z is a leaving group) in the presence of a base, the hydantoin derivative represented by formulae (B), (C) and (D) (wherein, X, Y, $R^1$, $R^2$, $R^3$ and $R^4$ have the same meanings as those mentioned above) is easily prepared by sequential or simultaneous introduction of $R^1$ group and $R^2$ group into the respective oxygen atom and nitrogen atom allows.

This reaction is preferably carried out in an organic solvent. This organic solvent may be exemplified by tetrahydrofuran, diethyl ether, dimethoxyethane, N,N-dimethylformamide, dimethylsulfoxide, acetonitrile, propionitrile acetone, methyl ethyl ketone, benzene, toluene and so forth.

The reaction proceeds in the presence of a base, for example, n-butyl lithium, sec-butyl lithium, methyl lithium, sodium hydride, potassium hydride, sodium carbonate, potassium carbonate, sodium bicarbonate, sodium acetate, potassium acetate, sodium hydroxide, potassium hydroxide, calcium hydroxide, and so forth.

The reaction temperature varies in accordance with the base and solvent used, but usually ranges from $-78°$ C. to $150°$ C.

Although a product can be isolated as a crystal by a general after-treatment after the reaction has been completed, it can, if necessary, be refined by silica gel column chromatography or recrystallization and so forth.

The hydantoin derivative represented by the aforementioned formula (A) can be prepared by the following method.

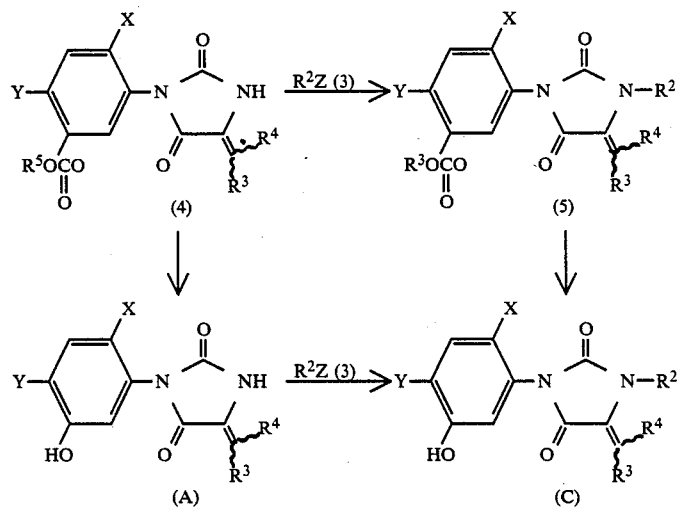

That is, the hydantoin derivative represented by formula (A) can be obtained by removal of a carbonate group in the presence of a base from the hydantoin derivative represented by the formula (4) (wherein X, Y, $R^3$ and $R^4$ denote the same as those mentioned above, and $R^5$ represents a lower alkyl group or an aralkyl group).

By a similar preparation method, the hydantoin derivative represented by formula (C) can be prepared. That is, the hydantoin derivative represented by formula (C) can be prepared by reacting the hydantoin derivative represented by formula (4) in the presence of a base with the compound $R^2 Z$ (wherein $R^2$ and Z denote the same as those mentioned above) represented by formula (3) so as to form the hydantoin derivative (5) (wherein X, Y, $R^2$, $R^3$, $R^4$ and $R_5$ denote the same as those mentioned above), the nitrogen atom of which is the alkyl form, followed by removal of the carbonate group by treatment with a base.

The compounds represented by formulae (2) and (3) which are the materials for preparing the compound according to the present invention is readily available or can be easily prepared from available raw materials. The compound represented by formula (2) is exemplified by alkyl halides such as methyl bromide, methyl iodide, ethyl bromide, ethyl iodide, propyl bromide, propyl iodide, isopropyl bromide, isopropyl iodide, butyl bromide, butyl iodide, isobutyl bromide, sec-butyl bromide, pentyl iodide, isopentyl iodide, hexyl iodide, 1-methyl pentyl bromide, 2-methyl pentyl iodide, octyl bromide, octyl iodide and dodecyl bromide.

It is also represented by cycloalkyl halides such as cyclopropyl bromide, cyclopentyl bromide, cyclohexyl bromide, and unsaturated halogenated compounds having a double bond, such as allylchrolide, allylbromide, methallylchrolide, methallylbromide, crotylbromide, crotylchloride, 3-bromol-butene, 3-bromo-3-methyl-1-butene, prenylbromide, 4-bromo-2-methyl-1-butene, 4-bromo-3-methyl-1-butene, 1-bromo-3-pentene, geranylbromide, 1,3-dichloropropene, 2,3-dichloropropene and 2,3-dibromo-1-butene.

Furthermore exemplified is unsaturated halogenated compounds having a triple bond such as propargyl chloride, propargyl bromide, propargyl iodide, 1-bromo-2-butyne, 1-chloro-2-butyne, 3-chloro-1-butyne, 3-bromo-3-methyl-1-butyne, 3-bromo-1-pentyne, 3-bromo-3-methyl-1-butyne, 3-chloro-3-methyl-1-butyne, 2-bromo-3-pentyne, 1-bromo-2-pentyne, 6-chloro-1-hexyne, 1-bromo-3-pentyne and 4-bromo-1-butyne.

Sulfonate and sulfate derivatives of unsaturated alcohols such as allyl alcohol, methallyl alcohol, 3-methyl-3-butene-1-ol , 2-methyl-3-butene-2-ol , prenyl alcohol, geraniol, nerol, propargyl alcohol, 1-butyne-3-ol, 3-methyl-1-butyne-3-ol or 1-butyne-4-ol and aliphatic alcohols such as methanol, ethanol, propanol and so forth can be used.

The compounds represented by formula (3) are exemplified by, for example, alkyl halides such as methyl bromide, methyl iodide, ethyl bromide, ethyl iodide, isopropyl bromide, isopropyl iodide, butyl bromide, butyl iodide, isobutyl bromide, sec-butyl bromide, pentyl iodide, isopentyl iodide, hexyl iodide, 1-methyl pentyl bromide, 2-methyl pentyl iodide, octyl bromide, octyl iodide and dodecyl bromide, and also by cylcoalkyl halides such as cyclopropyl bromide, cyclopentyl bromide and cyclohexyl bromide.

It is further exemplified by unsaturated halogenated compounds having a double bond, such as allyl chloride, allyl bromide, methallyl chloride, methallyl bromide, crotyl bromide, crotyl chloride, 3-bromo-1butene, 3-bromo-3-methyl-1-butene, prenyl bromide, 4-bromo-2-methyl-1-butene, 4-bromo-3-methyl-1-butene, 1-bromo-3-pentene, geranyl bromide, 1,3-dichloropropene, 2,3-dichloropropene, 2,3-dibromo-1-butene.

Furthermore, unsaturated halogenated compounds having a triple bond exemplified by propargyl chloride, propargyl bromide, propargyl iodide, 1-bromo-2-butyne, 1-chloro-2-butyne, 3-chloro-1-butyne, 3-bromo-1-butyne, 3-bromo-1-pentyne, 3-bromo-3-methyl-1-butyne, 3-chloro-3-methyl-1-butyne, 2-bromo-3-pentyne, 1-bromo-2-pentyne, 6-chloro-1-hexyne, 1-bromo-3-pentyne, 4-bromo-1-butyne can be used.

Sulfonate and sulfate derivatives of unsaturated alcohols such as allyl alcohol, methallyl alcohol, 3-methyl-3-butene-1-ol, 2-methyl-3-butene-2-ol, prenyl alcohol, geraniol, nerol, propargyl alcohol, 1-butene-3-ol, 3-methyl-1-butene-3-ol and 1-butene-4-ol, and aliphatic alcohol such as methanol, ethanol propanol and so forth, can be used.

The hydantoin derivative represented by formula (4) which is a precursor for preparation of the compound according to the present invention can be prepared, for example, by the following method.

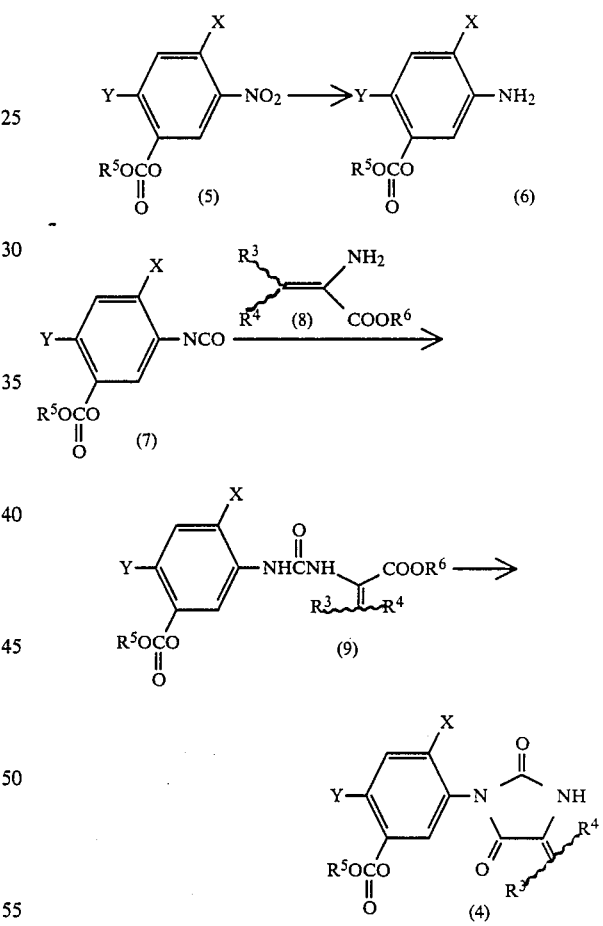

That is, the nitrobenzene derivative (5) (wherein X and Y represent the same as mentioned above, $R^5$ is lower alkyl group or an aralkyl group) is reduced with hydrogen in the presence of a catalyst such as platinum oxide, platinumcarbon or palladium-carbon and the like, so as to be made aniline derivative (6) (wherein X, Y and $R^5$ represent the same defined above) and is treated with a phosgen gas or trichloromethyl chloroformate whereby it can be converted into an isocianate derivative (7) (wherein X, Y and $R^5$ represent the same mentioned above). Then the urea derivative represented by formula (9) (wherein X, Y, $R^3$, $R^4$, $R^5$ and $R^6$ represent the same mentioned above) is obtained by reacting this isocyanate derivative (7) and α-amino-α,β-unsaturated carboxylic acid ester (8) (wherein $R^3$ and $R^4$ independently represent hydrogen atom or lower alkyl group, $R^6$ represent lower alkyl group). The hydantoin derivative represented by formula (4) can be obtained by treating the above m the presence of acid or base (see following example).

The urea derivative represented by formula (9) which is a material for the hydantoin derivative represented by formula (4) also can be prepared in the following method.

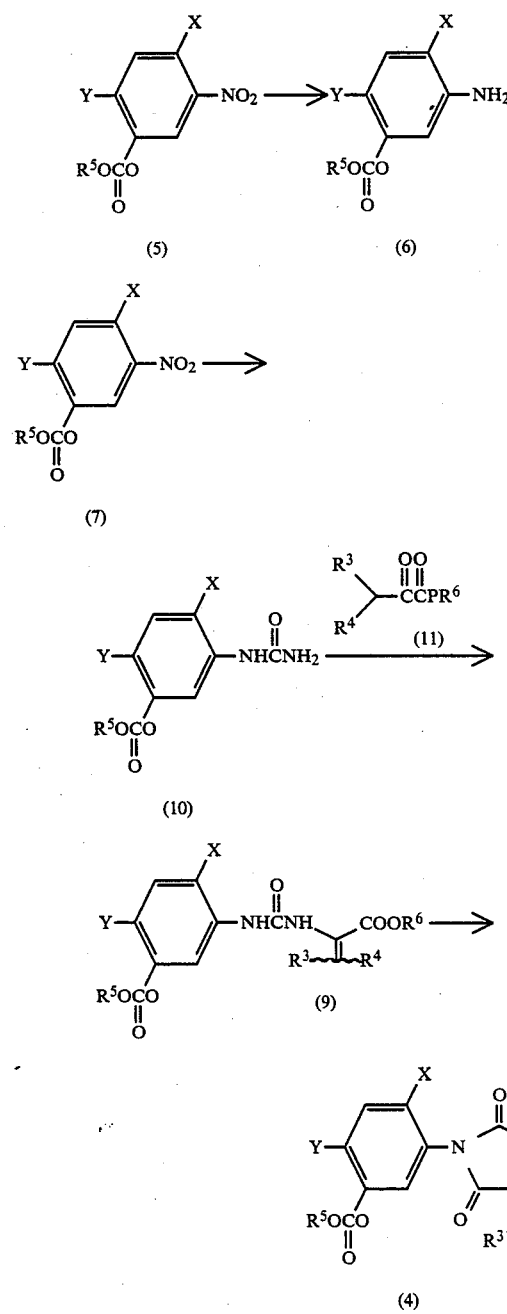

That is, the urea derivative (10) (wherein X, Y and $R^5$ denote the same mentioned above) which is obtained by reaction of the isocyanate derivative represented by the formula (7) which can be prepared in the aforesaid method from the aforementioned nitrobenzene derivative (5) and ammonia is reacted with α-ketocarboxylic acid ester represented by the formula (11) (wherein $R^3$, $R^4$ and $R^5$ denote the same mentioned above) in the presence of acid catalyst, whereby the urea derivative represented by the formula (9) can be obtained. The hydantoin derivative represented by the formula (4) can be obtained by treating this derivative in the presence of acid or base in the similar manner mentioned above (see the example below).

The example will now be described. The method of preparing the material which was used to prepare the compounds according to the present invention will be simultaneously described as a reference.

EXAMPLE 1

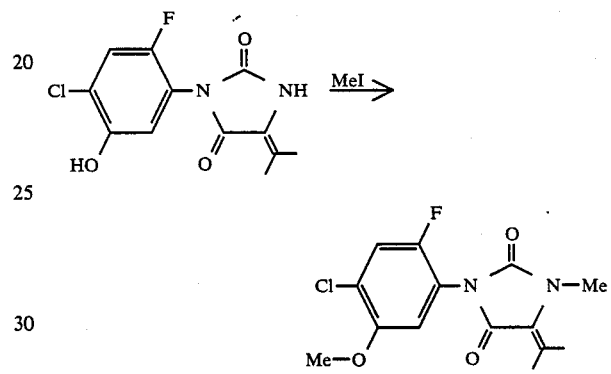

To a N,N-dimethylformamide solution (3 ml) of 3-(2'-fluoro-4'-chloro-5'-hydroxyphenyl)5-iso-propylidenehydantoin (25 mg, 91.7 μ mol) in a screw-capped test tube was added potassium carbonate (70 mg) and methyl iodide (100 μl), and the mixture was stirred at 40° C. for 9 hours. After completion of the reaction, the resulting mixture was quenched with a saturated ammonium chloride aqueous solution was added and extracted by means of ether (3 ml×3 times). The organic layer was washed with water (2 ml×3 times), and dried with anhydrous magnesium sulfate. After removal of the drying agent and condensation of the filtrate under reduced pressure, the white solids were isolated by filtration and identified as 1-methyl-3-(2'-fluoro-4'-chloro-5'-methoxyphenyl)-5-iso-propylidenehydantoin, and its yield was 22 mg (yield 80%).

EXAMPLE 2

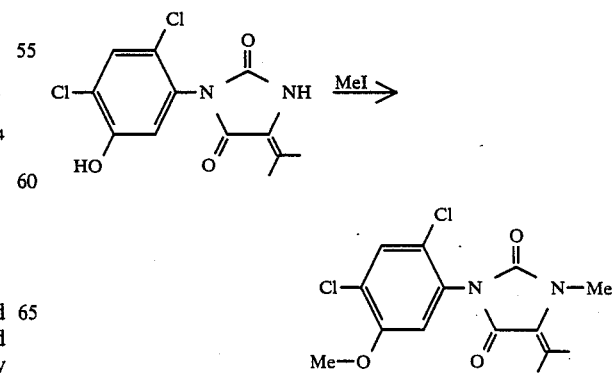

To an N,N-dimethylformamide (20 ml) of 3-(2',4'-dichloro-5'-hydroxyphenyl)5-isopropylidenehydantoin (200 mg, 0.66 mmol) was added potassium carbonate (914 mg) and methyl iodide (4 g), and the mixture was stirred at 40° C. for 9 hours. After completion of the reaction, the resulting mixture was quenched with 1N-hydrochloric acid was added for acidification, and extracted with ether (20 ml×3 times). The organic layer was washed with water (10 ml×3 times), and dried over anhydrous magnesium sulfate. After removal of the drying agent, a colorless transparent oily product was obtained by condensation of the filtrate under reduced pressure. A white solid (213 mg, yield 98%) was obtained by filtration after addition of ethanol and cooling at −78° C. This product was confirmed to be 1-methyl-3-(2', 4'-dichloro-5'-methoxyphenyl)-5-isopropylidenehydantoin by means of spectrum analyses.

EXAMPLE 3

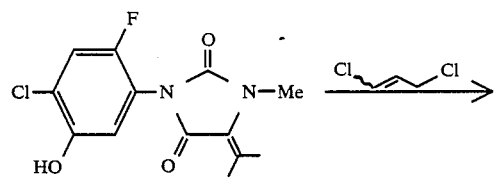

to a N,N-dimethylformamide solution (25 ml) of 1-methyl-3-(2'-fluoro-4'-chloro-5'-hydroxyphenyl)-5-isopropylidenehydantoin (965 mg, 3.2 mmol) was added potassium carbonate (1.0 g) and 1,3-dichloropropene (2.8 ml), and the mixture was stirred at 40° C. for 4 hours. After completion of the reaction, the resulting mixture was quenched with 1N-hydrochloric acid for acidification, and extracted with ether (10 ml×3 times). After the organic layer was washed with water (5 ml×3 times) and dried over anhydrous magnesium sulfate. After removal of the drying agent, the yellow oily product (1.12 g) was obtained by condensation of the filtrate under reduced pressure. It was refined with silica gel column chromatography (benzene/ethyl acetate×4/1) to give yellow product (415 mg, yield 36%) of 1-methyl-3-{2'-fluoro-4'-chloro-5'-(3''-chloro-2''-propenyloxy)phenyl}-5-isopropylidenehydantoin. This product can be purified as a light yellow solid by recrystallization from ethanol.

EXAMPLE 4

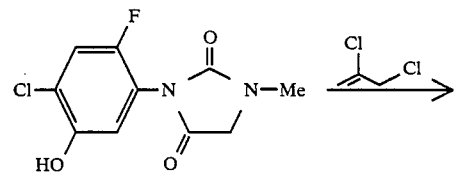

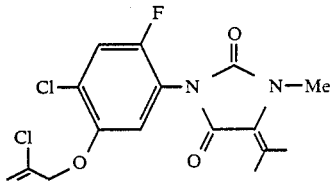

To an N,N-dimethylformamide solution (20 ml) of 1-methyl-3-(2'-fluoro-4'-chloro-5'-hydroxyphenyl)5-isopropylidenehydantoin (500 mg, 1.7 mmol) was added potassium carbonate (1.14 g) and 2,3-dichloropropene (1.54 ml), and the mixture was stirred at 40° C. for 5 hours. After the reaction was completed, the resulting mixture was quenched with 1N-hydrochloric acid and extracted with ether (10 ml×3 times). The organic layer was washed with water (5 ml×3 times) and dried over anhydrous magnesium sulfate. After removal of the drying agent an yellow oily product was obtained by condensation of the ethereal solution under reduced pressure. A solid (135 mg, yield 22%) was obtained by filtration after addition of methanol and cooling at −78° C. This product was confirmed to be 1-methyl-3-(2',4-dichloro-5-(2''-chloro-2''-propenyloxy)phenyl}-5-isopropylidenehydantoin by observation of spectrum analyses.

EXAMPLE 5

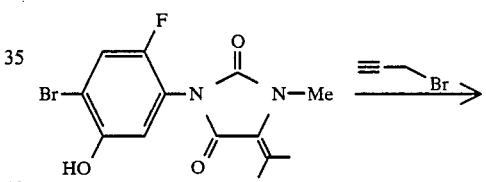

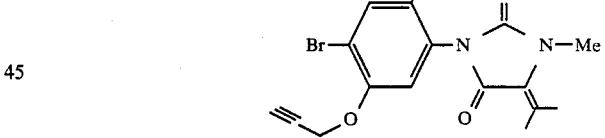

To an N,N-dimethylformamide solution (10 ml) of 1-methyl-3-(2'-fluoro-4'-bromo-5'-hydroxyphenyl)-5-isopropylidenehydantoin (101 mg, 0.34 mmol) was added potassium carbonate (200 mg) and propargylbromide (350 mg), and the mixture was stirred at 40° C. for 5 hours. After completion of the reaction, the reaction mixture was quenched with 1N-hydrochloric acid for acidification, and extracted with ether (10 ml×3 times). The organic layer was washed with water (2 ml×3 times) and dried over anhydrous magnesium sulfate. After removal of the drying agent a colorless transparent oily product was obtained by condensation of the filtrate under reduced pressure. A white solid (60 mg, yield 52%) was obtained by filtration after addition of ethanol and cooling at −78° C. This product was confirmed to be 1-methyl-3-(2'-fluoro-4'-bromo-5'-propargyloxyphenyl)-5-isopropylidenehydantoin by means of spectrum analyses.

EXAMPLE 6

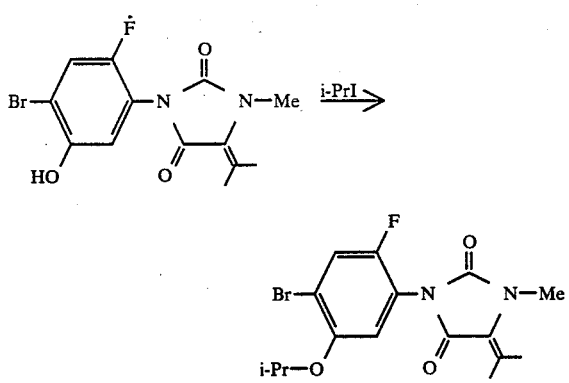

To an acetonitrile solution (15 ml) of 1-methyl-3-(2'-fluoro-4'-bromo-5'-hydroxyphenyl)-5-isopropylidenehydantoin (130 mg, 0.38 mmol) was added potassium carbonate (275 mg) and isopropyliodide (650 mg) and the mixture was stirred at 40° C. for 20 hours. After completion of the reaction, the reaction mixture was quenched with 1N-hydrochloric acid for acidification, and the reaction mixture was extracted with ether (10 ml×3 times). The organic layer was washed with water (5 ml×3 times), then dried over anhydrous magnesium sulfate. After removal of the drying agent an brown oily product was obtained by condensation of the filtrate under reduced pressure. A colorless solid (70 mg, yield 47%) was obtained by filtration of the deposit after addition of ethanol and cooling at −78° C. This product was confirmed to be 1-methyl-3-(2'-fluoro-4'-bromo-5'-isopropoxylphenyl)-5-isopropylidenehydantoin by means of spectral analyses.

EXAMPLE 7

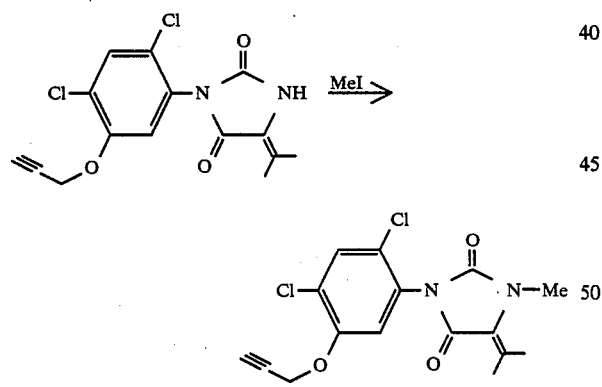

To an N,N-dimethylformamide solution (20 ml) of 3-(2',4'-dichloro-5'-propargyloxyphenyl)-5-isopropylidenehydantoin (150 mg, 0.44 mmol) was added potassium carbonate (300 mg) and methyl iodide (630 mg), and then the mixture was stirred at 60° C. for 14 hours. After completion of the reaction, the reaction mixture was quenched with 1N-hydrochloric acid for acidification, and extracted by means of ether (10 ml×3 times). The organic layer was then washed with water (5 ml×3 times) and dried over anhydrous magnesium sulfate. After removal of the drying agent a light yellow oily product was obtained by condensation of the filtrate under reduced pressure. A white solid (124 mg, yield 80%) was obtained by filtration after addition of ethanol and cooling at −78° C. This product was confirmed to be 1-methyl-3-(2',4'-dichloro-5'-propargyloxyphenyl)-5-isopropylidenehydantoin by spectral analyses.

EXAMPLE 8

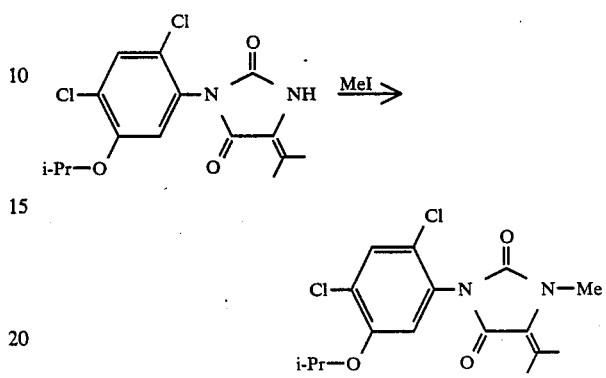

To an N,N-dimethylformamide solution (15 ml) of 3-(2',4'-dichloro-5'-isopropoxyphenyl)-5-isopropylidenehydantoin (140 mg, 0.41 mmol) was added potassium carbonate (283 mg) and methyl iodide (600 mg), and then the mixture was stirred at 50° C. for an hour. After completion of the reaction, the reaction mixture was quenched with 1N-hydrochloric acid for acidification and extracted by means of ether (5 ml×3 times). The organic layer was washed with water (3 ml×3 times) and dried over anhydrous magnesium sulfate. After removal of the drying agent a colorless transparent oily product (120 mg, yield 83%) was obtained by condensation of the filtrate under reduced pressure. This product was confirmed to be 1-methyl-3-(2',4'-dichloro-5'-isopropoxyphenyl)-5-isopropylidenehydantoin by means of spectral analyses.

EXAMPLE 9

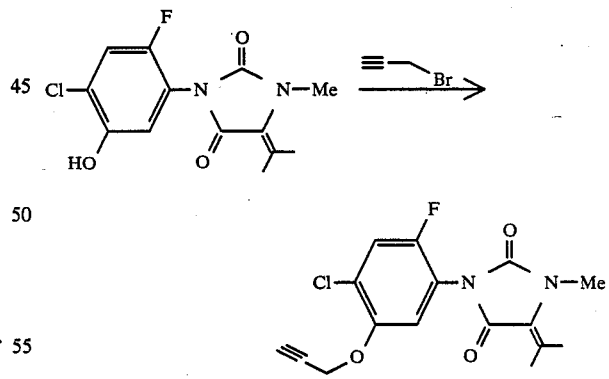

To an acetonitrile solution (30 ml) of 1-methyl-3-(2'-fluoro-4'-chloro-5'-hydroxyphenyl)-5-isopropylidenehydantoin (900 mg, 3.0 mmol) was added potassium carbonate (1.02 g) and propargyl bromide (2.6 ml), and then the mixture was stirred at 40° C. for 4 hours. After completion of the reaction, the reaction mixture was quenched with saturated ammonium chloride aqueous solution for acidification, and extracted with ether (10 ml×3 times). The organic layer was washed with water (5 ml×3 times) and dried over anhydrous magnesium sulfate. After removal of the drying agent the white solid was obtained by concentration of the filtrate under reduced pressure. Then white crystal (264 mg, yield 26%) recrystallized from ethanol was obtained by filtration. This product was confirmed to be 1-methyl-3-(2'-fluoro-4'-chloro-5'-propargyloxyphenyl)-5-isopropylidenehydantoin by means of spectral analyses.

EXAMPLE 10

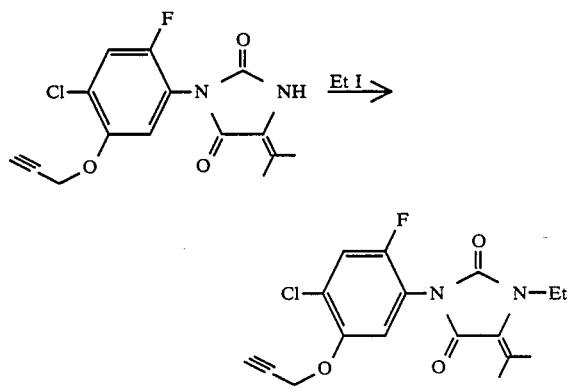

To an N,N-dimethylformamide solution (15 ml) of 3-(2'-fluoro-4'-chloro-5'-propargyloxyphenyl)-5-isopropylidene hydantoin (113 mg, 0.35 mmol) was added potassium carbonate (246 mg) and ethyl iodide (550 mg), and then the mixture was stirred at 50° C. for 5 hours. After the reaction was completed, the reaction mixture was quenched with 0.1N-hydrochloric acid. After cooling, the colorless solid deposited was isolated by filtration. This product (93 mg, yield 77%) was confirmed to be 1-ethyl-3-(2'-fluoro-4'-chloro-5'-propargyloxyphenyl)-5-isopropylidenehydantoin by means of spectral analyses.

EXAMPLE 11

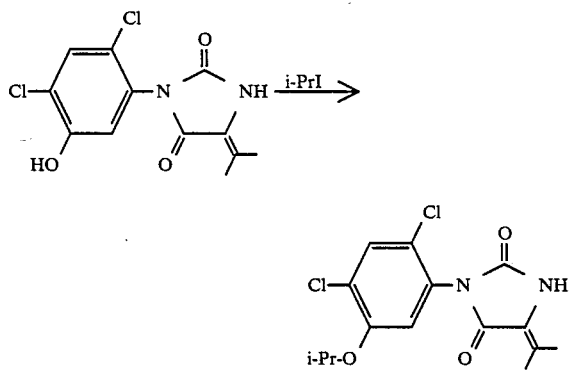

To an acetonitrile solution (25 ml) of 3-(2',4'-dichloro-5'-hydroxyphenyl)-5-isopropylidenehydantoin (300 mg, 1.0 mmol) was added potassium carbonate (650 mg) and isopropyl iodide (1.7 g), and then the mixture was stirred at 50° C. for 2 hours. After completion of the reaction, the reaction mixture was quenched with 1N-hydrochloric acid for acidification, and extracted with ether (20 ml×3 times). The organic layer was washed with water (10 ml×3 times) and dried over anhydrous magnesium sulfate. After removal of the drying agent a colorless oily product (330 mg) was obtained by condensation of the filtrate under reduced pressure. A white solid (290 mg) was then isolated by way of recrystallization from chloroform-hexane. This product was confirmed to be 3-(2',4'-dichloro-5'-isopropoxyphenyl)-5-isopropylidenehydantoin by spectral analyses.

EXAMPLE 12

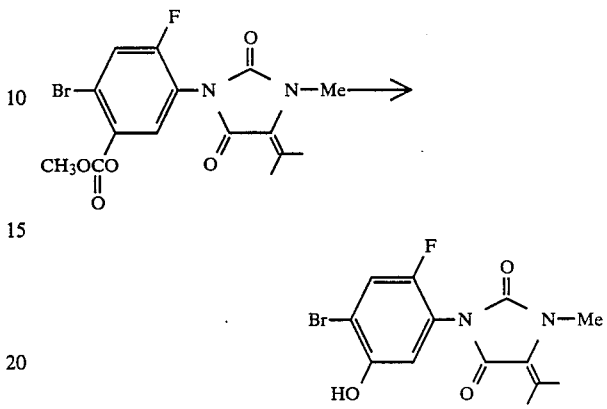

To a methanol solution (10 ml) of 1-methyl-3-(2'-fluoro-4'-bromo-5'-methoxycarbonyloxyphenyl)-5-isopropylidenehydantoin (1.03 g, 2.57 mmol) was added potassium carbonate (50 mg), and then the mixture was stirred at 50° C. for 2 hours. After completion of the reaction, the reaction mixture was quenched with 1N-hydrochloric acid for acidification, and extracted with ether (40 ml×3 times). The organic layer was washed with water (20 ml×3 times), and then dried over anhydrous magnesium sulfate. After removal of the drying agent a yellow oily product (1.04 g) was obtained by condensation of the filtrate under reduced pressure. It was purified by silica gel column chromatography (ethyl acetate/hexane=1/1) so as to obtain an oily product (430 mg). This product was confirmed to be 1-methyl-3-(2'-fluoro-4'-bromo-5'-hydroxyphenyl)-5-isopropylidenehydantoin, which was essentially pure.

Then, it was purified by silica gel column chromatography (ethyl acetate/chloroform=½) so as to obtain a colorless transparent oily product (319 mg, yield 36%).

EXAMPLE 13

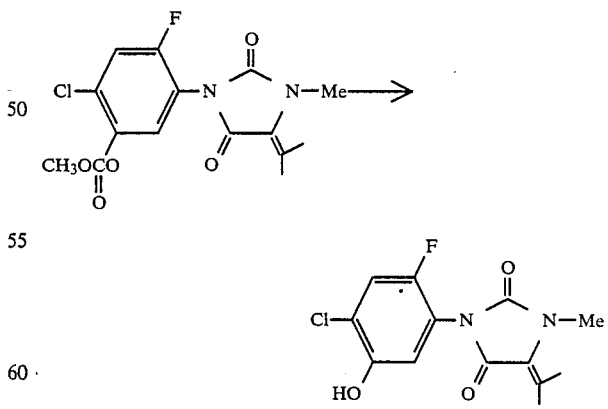

To a methanol solution (59 ml) of 1-methyl-3-(2'-fluoro-4'-chloro-5'-methoxycarbonyloxyphenyl)-5-isopropylidenehydantoin (6.5 g, 17.6 mmol) was placed was added potassium carbonate (2.5 g), and the mixture was stirred at 40° C. for 12 hours. After the reaction was completed, the resulting mixture was quenched with saturated ammonium chloride aqueous solution and extracted with ether (30 ml×3 times). The organic layer was washed with water (10 ml×3 times) and dried over anhydrous magnesium sulfate. After removal of the drying agent brown oily product was obtained by condensation of the filtrate under reduced pressure. Then it was purified by silica gel column chromatography (eluted with ethylacetate). This product (5.5 g) was confirmed to be 1-methyl-3-(2'-fluoro-4'-chloro-5'-hydroxyphenyl)-5-isopropylidene hydantoin by spectral analyses.

EXAMPLE 14

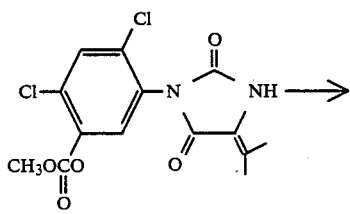

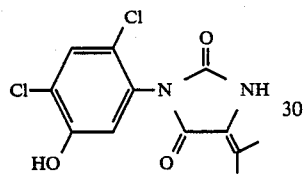

To a methanol solution (40 ml) of 3-(2',4'-dichloro-5'-methoxycarbonyloxyphenyl)-5-isopropylidenehydantoin (2.3 g, 6.4 mmol) was added potassium carbonate (500 mg), and then the mixture was stirred at 60° C. for an hour. After completion of the reaction, the reaction mixture was quenched with 1N-hydrochloric acid for acidification, and extracted with ether (20 ml×3 times). The organic layer was washed with water (10 ml×3 times) and dried over anhydrous magnesium sulfate. After removal of the drying agent a light yellow oily product (1.93 g) was obtained by condensation of the filtered under reduced pressure. Ether was added to the resulting pale yellow oil to precipitate white crystals of the desired product. These crystals (1.02 g) isolated by filtration was identified as 3-(2',4'-dichloro-5'-hydroxyphenyl)-5-isopropylidenehydantoin by spectral analyses. Then a white solid (0.9 g) was also obtained by condensation of the mother liquor and addition of ether. The reaction proceeded in a quantative manner.

EXAMPLE 15

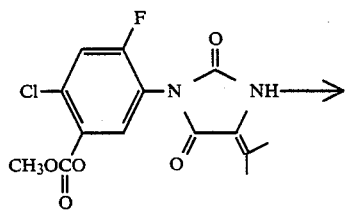

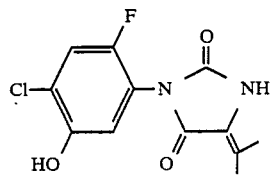

To a methanol solution (5 ml) of 3-(2'-fluoro-4'-chloro-5'-methoxycarbonyloxyphenyl)-5-isopropylidenehydantoin (110 mg, 0.31 mmol) in a screw-capped test tube was added potassium carbonate (54 mg), and then the mixture stirred at 40° C. for 3 hours. After completion of the reaction, the reaction mixture was quenched with saturated ammonium chloride aqueous solution for acidification, and extracted with ether (2 ml×3 times). The organic layer was washed with water (1 ml×3 times) and dried over anhydrous magnesium sulfate. After removal of the drying agent brown oily product (67 mg, yield 77%) was obtained by condensation of the filtrate under reduced pressure. This product was confirmed to be 3-(2'-fluoro-4'-chloro-5'-hydroxyphenyl)-5-isopropylidenehydantoin by means of spectral analyses.

EXAMPLE 16

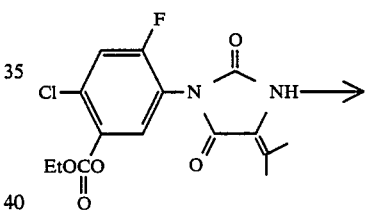

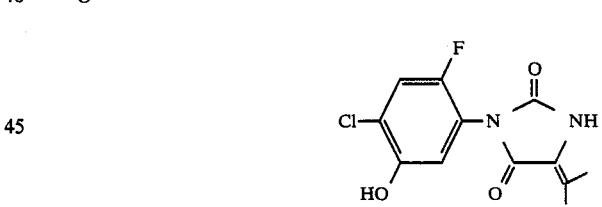

A methanol solution (20 ml) of 3-(2'-fluoro-4'-chloro-5'-ethoxylcarbonyloxyphenyl)-5-isopropylidene hydantoin (204 mg, 0.57 mmol) and sodium carbonate (50 mg) was stirred at 40° C. for 3 hours. After completion of the reaction, the reaction mixture was quenched with saturated ammonium chloride aqueous solution extracted with ether (5 ml×3 times). The organic layer was washed with water and dried over anhydrous magnesium sulfate. After removal of the drying agent by filtration, a brown oily product was obtained by condensation of the filtrate under reduced pressure. After addition of ether, a white crystal (162 mg) was precipitated and isolated by filtration. This product was confirmed to be 3-(2'-fluoro-4'-chloro-5'-hydroxyphenyl)-5-isopropylidenehydantoin by means of spectral analyses.

EXAMPLE 17

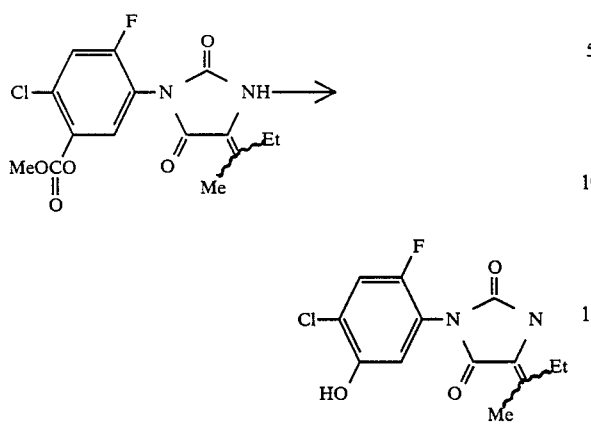

To a methanol solution (40 ml) of 3-(2'-fluoro-4'-chloro-5'-methoxycarbonyloxyphenyl)-5-(2"-butylidene)-hydantoin (1.02 g, 3.0 mmol) was added potassium carbonate (230 mg) and then the mixture was stirred at room temperature for 15 hours. After completion of the reaction, the reaction mixture was quenched with 1N-hydrochloric acid, and extracted with ether (1.0 ml×3 times). The organic layer was washed with water (5 ml×3 times), and then dried over anhydrous magnesium sulfate. After removal of the drying agent by filtration a colorless transparent oily product (895 mg) was obtained by condensation of the filtrate under reduced pressure. This product was confirmed to be a substantially pure 3-(2'-fluoro-4'-chloro-5'-hydroxyphenyl)-5-(2"-butylidene)hydantoin by means of spectral analyses.

EXAMPLE 18

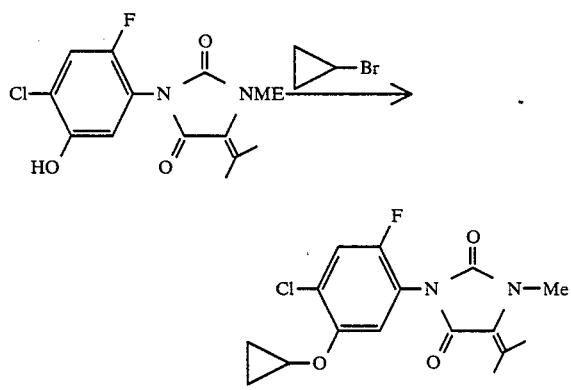

To a N,N-dimethylformamide solution (20 ml) of 1-methyl-3-(2'-fluoro-4'-hydroxyphenyl)-5-isopropylidenehydantoin (200 mg, 0.63 , mmol) was added potassium carbonate (450 mg) and then the mixture was stirred at room temperature for 30 minutes. Then cyclopropylbromide was added and reacted at room temperature for further 18 hours. After completion of the reaction, the reaction mixture was quenched with 1N-hydrochloric acid and extracted with ether (5 ml×3 times). The organic layer was washed with water, dried over anhydrous magnetic sulfate. After removal of the dying agent by filtration a light yellow oily product was obtained by condensation of the filtrate under reduced pressure. It was then purified by means of silica gel column chromatography. This product was confirmed to be 1-methyl-3-(2'-fluoro-4'-chloro-5'-cycropropyloxyphenyl)-5-isopropylidenehydantoin (110 mg, 49%) by means of spectral analyses.

EXAMPLE 19

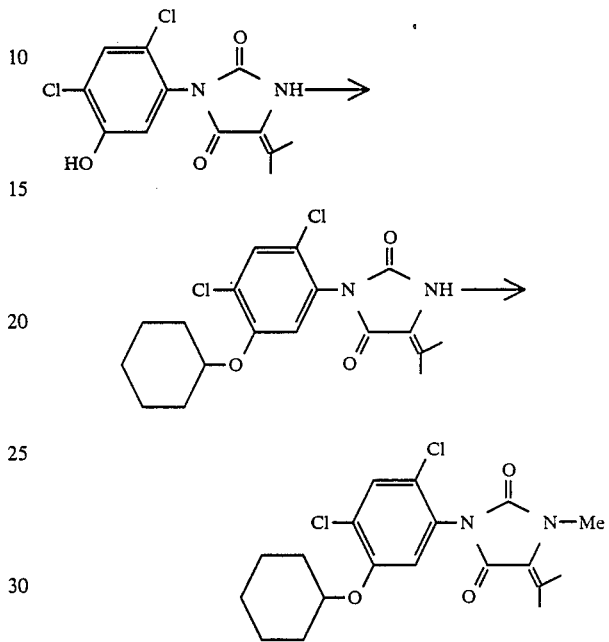

To a acetonitrile solution (5 ml) of 3-(2',4'-dichloro-5'-hydroxyphenyl)-5-isopropylidenehydantoin(105 mg, 0.35 mmol) in a screw-capped test tube was added potassium carbonate (60 mg) and cychohexylbromide and the mixture was reacted at 50° C. for 24 hours. After completion of the reaction, the mixture was condensed under reduced pressure and the solvent and excess cychohexylbromide were removed. Then dimethylformamide (5 ml) and methyliodide (200 mg) was added to the resulting mixture and stirred at 40° C. for 2 hours. After completion of the reaction, the resulting mixture was quenched with 0.1N hydrochloric acid and extracted with ether (2 ml×3 times). The organic layer was washed with water and dried over anhydrous magnesium sulfate. After removal of the drying agent the filtrate was condensed under reduced pressure to give an oily compound. It was then purified by silica gel column chromatography. This product (60 mg) was confirmed to be 1-methyl-3-(2',4'-dichloro-5'-cyclohexyloxyphenyl)-5-isopropylidenehydantoin by means of spectral analyses. It was recrystallized from ethanol and the desired white solid (20 mg, yield 14%) was obtained by filtration.

EXAMPLE 20

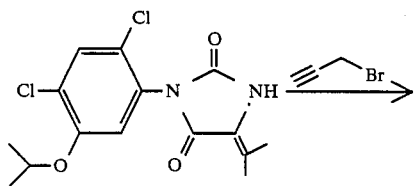

-continued

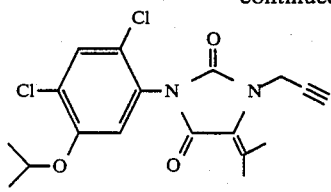

To a N,N-dimethylformamide solution (20 ml) of 3-(2', 4'-dichloro-5'-isopropoxyphenyl)-5-isopropylidenehydantoin (152 mg, 0.446 mmol) was added potassium carbonate (362 mg) and propargylbromide (600 mg) and then mixture was stirred at room temperature for 13 hours. After completion of the reaction, the reaction mixture was quenched 1N-hydrochloric acid and extracted with ether (5 ml×3 times). The organic layer was washed with water (3 ml×3 times), then dried over anhydrous magnesium sulfate. After removal of the drying agent by filtration a light yellow oily product (170 mg) was obtained by condensation of the filtrate reduced pressure. This product was confirmed to be 1-propargyl-3-(2',4'-dichloro-5'-isopropoxyphenyl)-5-isopropylidenehydantoin by means of spectral analyses. The product was quantatively yielded.

EXAMPLE 21

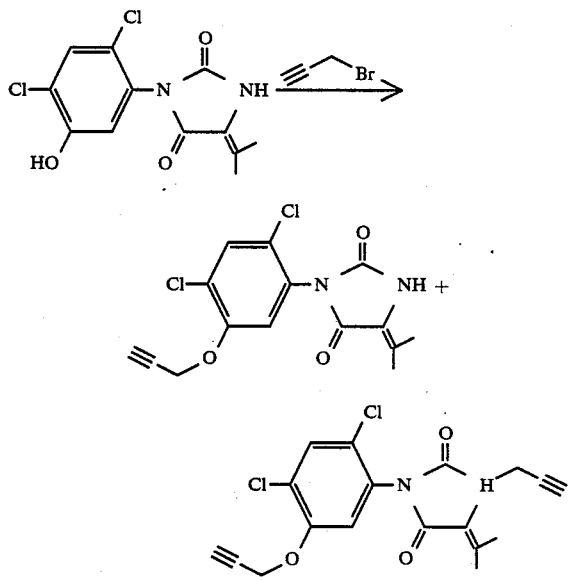

To a N,N-dimethylformamide solution (840 ml) of 3-(2',4'-dichloro-5'-hydroxyphenyl)-5-isopropylidenehydantoin (970 mg, 3.22 mmol) was added and potassium carbonate (702 mg) and propargylbromide (2.9 ml) and the mixture was stirred at 50° C. for 4 hours and at 80° C. for further 8 hours. After completion of the reaction, the resulting mixture was quenched with 1N-hydrochloric acid and extracted with ether (20 ml×3 times). The organic layer was washed with water, then dried over anhydrous magnesium sulfate. After removal of the drying agent by filtration a light yellow oily product (1.95 g) was obtained by condensation of the filtrate under reduced pressure. After addition of ether and cooling, a white solid deposited was isolated by filtration. This product (193 mg) was confirmed to be 3-(2',4', dichloro-5'-propargyloxyphenyl)-5-isopropylidenehydantoin in which a propargyl group was introduced into the hydroxyl group at 5-position on a phenyl ring by observation of ¹H-NMR spectrum analysis. The filtrate was then condensated whereby white crystal (694 mg, yield 57%) of 1-propargyl-3-(2',4'-dichloro-5'-propargyloxyphenyl)-5-isopropylidenehydantoin in which the propargyl group was introduced on the nitrogen atom at the 1-position on a hydantoin ring was obtained by recrystallization from chloroform/hexane.

EXAMPLE 22

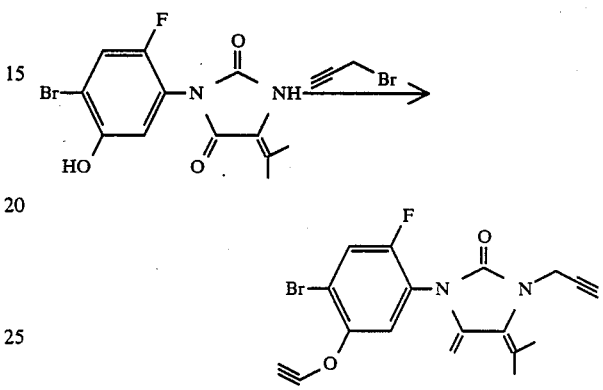

To an acetonitrile solution (10 ml) of 3-(2'-fluoro-4'-bromo-5'-hydroxyphenyl)-5-isopropylidenehydantoin (210 mg, 0.64 mmol) was added potassium carbonate (470 mg) and propargylbromide (800 mg) and then the mixture was stirred at 40° C. for 4 hours. After completion of the reaction, the resulting mixture was quenched with 1N-hydrochloric acid and then left at room temperature. The crystal precipitated was isolated by filtration. This product (240 mg, yield 93%) was confirmed to be 1-propargyl-3-(2'-fluoro-4'-bromo-5'-propargyloxyphenyl)-5-isopropylidenehydantoin by means of spectral analyses.

EXAMPLE 23

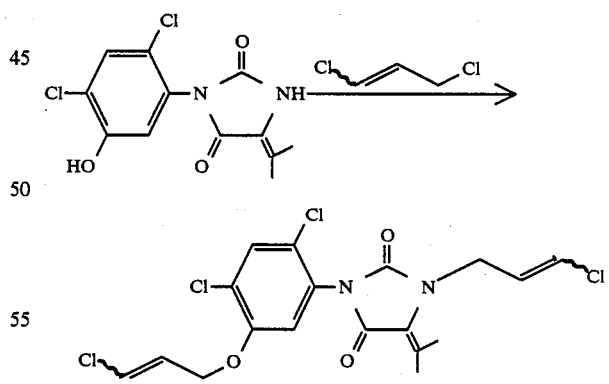

To an acetonitrile solution (840 ml) of 3-(2',4'-dichloro-5'-hydroxyphenyl)-5-isopropylidenehydantoin (1.0 g, 3.3 mmol) was added potassium carbonate (2.4 g) and 1,3-dichloropropene (3.7 g) and then the mixture was stirred at 60° C. for 10 hours. After completion of the reaction, the solid precipitated was filtered, washed with water (20 ml×3 times), and dried over anhydrous magnesium sulfate. After removal of the drying agent by filtration a yellow oily product (1.62 g) was obtained by condensation of the filtrate under reduced pressure.

It was then isolated and purified by silica gel column chromatography. The desired product of 1-(3'-chloro-2'-propenyl)-3-{2", 4"-dichloro-5"-(3"'-chloro-2"'-propenyloxyphenyl}-5-isopropylidenehydantoin (1.41 g, yield 94%) was obtained. This product is a mixture of four stereoisomers with respect to the sterochemistry of the double bonds of chloropropenyl groups on the nitrogen atom at 1-position of hydantoin ring and on the oxygen atom at 5'-position on the phenyl ring. E-Z form, Z-E form and E-E form of them were isolated by column chromatography or recrystallization, and the structure thereof was confirmed by measurement of 400 MHz $^1$H-NMR spectrum.

EXAMPLE 24

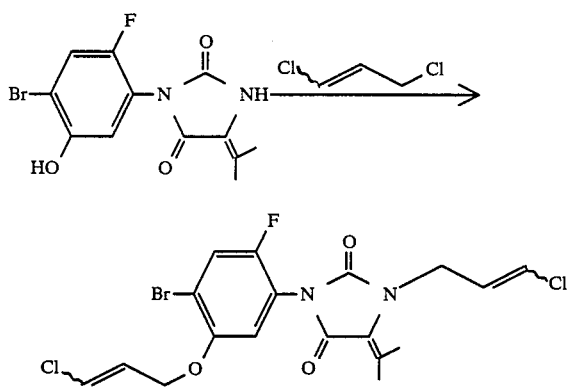

To an acetonitrile solution (810 ml) of 3-(2'-fluoro-4'-bromo-5'-hydroxyphenyl)-5-isopropylidenehydantoin (210 mg, 0.64 mmol) was added potassium carbonate (470 mg) and 1,3-dichloropropene (710 mg) and then the mixture was stirred at 80° C. for 3 hours. After completion of the reaction, the resulting mixture was quenched with 1N-hydrochloric acid and extracted with ether (5 ml×3 times). The organic layer was washed with water (3 ml×3 times), then dried over anhydrous magnesium sulfate. After removal of the drying agent by filtration a yellow oily product (310 mg) was obtained by condensation of the filtrate under reduced pressure. It was then isolated and purified by silica gel column chromatography (ethyl acetate/hexane=½). 1(3'-Chloro-2'-propenyl)-3-{2"-fluoro-4"-bromo-5"-(3"'-chloro-2"'-propenyloxy)phenyl}-5-isopropylidenehydantoin (202 mg, yield 58%) was obtained. This product is a mixture of stereo isomers with respect to the stereochemistry of olefins of chlorophenyl group on the nitrogen atom and on the oxygen atom. E-E form of them was isolated and purified by column chromatography, and its structure was confirmed by 400 Hz $^1$H-NMR spectrum.

EXAMPLE 25

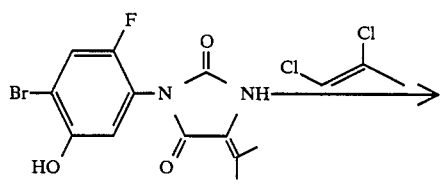

-continued

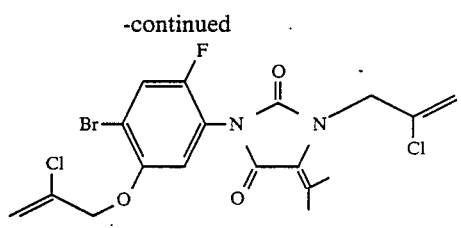

To an acetonitrile solution (12 ml) 3-(2'-fluoro-4'-bromo-5'-hydroxyphenyl)-5-isopropylidenehydantoin (214 mg, 0.65 mmol) was added potassium carbonate (450 mg) and 2,3-dichloropropene (750 mg) and then the mixture was stirred at 50° C. for 5 hours. After completion of the reaction, the resulting mixture was quenched with 0.1N hydrochloric acid and extracted with ether (4 ml×3 times). The organic layer was washed with water (2 ml×3 times), then dried over anhydrous magnesium sulfate. After removal of the drying agent by filtration a yellow oily product was obtained by condensation of the filtrate under reduced pressure. It was then isolated and refined by silica gel column chromatography (ethyl acetate/hexane=½), and light yellow oily product (230 mg, yield 74%) of 1-(2'-chloro-2'-propenyl)-3-{2"-fluoro-4'-bromo-5'-(2"'-chloro-2"'-propenyloxy)phenyl}-5-isopropylidenehydantoin was obtained.

EXAMPLE 26

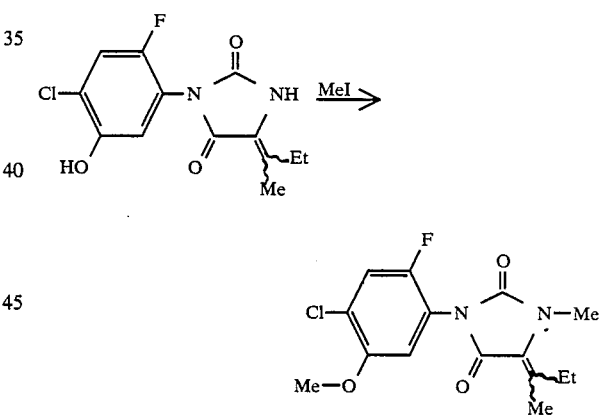

To an N,N-dimethylformamide solution (20 ml) of 3-(2'-fluoro-4'-chloro-5'-hydroxyphenyl)-5-(2"-butylidene)-hydantoin (170 mg, 0.57 mmol) potassium carbonate (170 mg) and methyliodide (500 μl) and the mixture was stirred at room temperature for 2 hours. After the reaction was completed, the resulting mixture was quenched with 3N-hydrochloric acid and was extracted with ether (10 ml×3 times). The organic layer was washed with water (5 ml×2 times) and dried with anhydrous magnesium sulfate. After removal of the drying agent by filtration, a colorless oily product (180 mg, yield 97%) of 1-methyl-3-(2'-fluoro-4'-chloro-5'-methoxyphenyl)-5-(2"-butylidene)hydantoin was obtained by condensation of the filtrate under reduced pressure. This product was purified by silica gel chromatography to give a light yellow oily product.

COMPARATIVE EXAMPLE 1

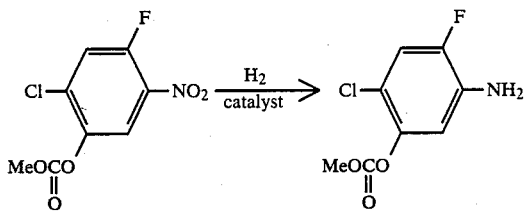

Platinum dioxide (1.5 g) was added to a solution of 2-fluoro-4-chloro-5-methoxycarbonyloxynitrobenzene (52.1 g, 0.24 mol) and the mixture was reacted in normal atmospheric pressure of hydrogen until absorption of a hydrogen gas was stopped. After completion of the reaction, the catalyst was filtered off. The solvent was then removed by distillation from a light yellow transparent filtrate to give a light brown oily product. This product was confirmed to be substantially pure 2-fluoro-4-chloro-5-methoxycarbonyloxyaniline by means of spectral analyses. This product can be purified by silica gel chromatography, though it can be used in the subsequent reaction without purification.

$^1$H-NMR (CDCl$_3$, TMS, ppm): δ 3.86 (3H,s), 4.13 (2H,br s), 6.48 (1H,d,J$_{HF}$=8 Hz), 6.92 (1H,d,J$_{HF}$=10 Hz)

COMPARATIVE EXAMPLE 2

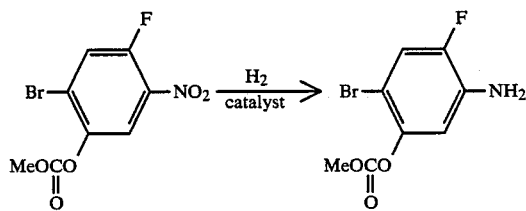

Platinum dioxide (1.0 g) was added to a solution of 2-fluoro-4-bromo-5-methoxycarbonyloxinitrobenzene (30.4 g, 0.1 mol) in ethanol (300 ml) and the solution was stirred in normal atmospheric pressure of hydrogen until absorption of hydrogen was terminated. After completion of the reaction, the catalyst was removed by filtration and the solvent was removed by distillation from the filtrate to give a brown solid (28.0 g) of 2-fluoro-4-bromo-5-methoxycarbonyloxianiline.

$^1$H-NMR (CCl$_4$, TMS, ppm): δ 3.83 (3H,s), 5.01 (2H,br s), 6.63 (1H,d,J$_{HF}$=7.6 Hz), 7.06 (1H,d,J$_{HF}$=9.8 Hz)

COMPARATIVE EXAMPLE 3

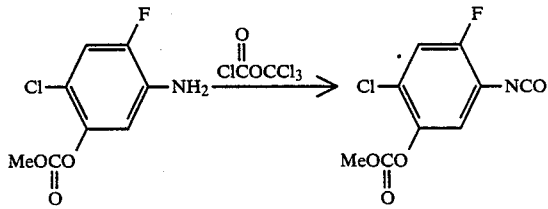

A solution of trichloromethyl chloroformate (19 ml, 158 mmol) in ethyl acetate (200 ml) was charged into a 500 ml-three neck flask equipped with a dropping funnel and a distillation apparatus and a solution of 2-fluoro-4-chloro-5-methoxycarbonyloxianiline (21.9 g, 100 mmol) in ethyl acetate (100 ml) was added dropwise in 20 minutes. After completion of addition, the mixture was heated at 80° C. and ethyl acetate was distilled off. After cooling, carbon tetrachloride (150 ml) was added and allowed the mixture to stand overnight. After removal of indissolved substances by filtration, the solvent was distilled off from filtrate under reduced pressure, whereby light brown solid of 2-fluoro-4-chloro-5-methoxycarbonyloxyphenyl isocyanate (20.6 g, yield 84%) was obtained.

$^1$H-NMR (CDCl$_3$, TMS, ppm): δ 3.88 (3H,s), 6.97 (1H,d), 7.37 (1H,d)

IR (KBr disk, cm$^{-1}$): 2260, 1770

COMPARATIVE EXAMPLE 4

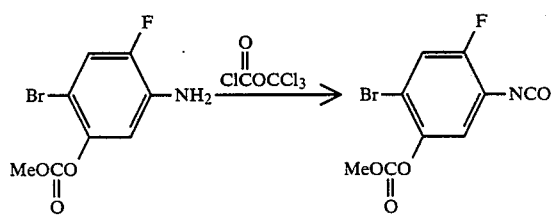

A solution of trichloromethyl chloroformate trichloromethyl (15 ml, 125 mmol) in ethyl acetate was charged into a 500 ml-three neck flask equipped with a dropping funnel and distillation apparatus and, a solution of 2-fluoro-4-bromo-5-methoxycarbonyloxyaniline (28.0 g,113 mmol) in ethyl acetate (100 ml) was added dropwise over 20 minutes. After dropping, the mixture was heated at 80° C. and ethyl acetate was removed by distillation. After cooling, carbon tetrachloride (150 ml) was added and the undissolved substances were removed by filtration. The solvent was then removed from the filtrate by distillation under reduced pressure, whereby a brown solid of 2-fluoro-4-bromo-5-methoxycarbonyloxyphenyl isocyanate (29.1 g, yield 94%) was obtained.

$^1$H-NMR (CCl$_4$, TMS, ppm): δ 3.87 (3H,s), 6.89 (1H,d, J$_{HF}$=6.8 Hz), 7.31 (1H,d,J$_{HF}$=8.6 Hz)

IR (KBr disk, cm$^{-1}$): 2260, 1770

COMPARATIVE EXAMPLE 5

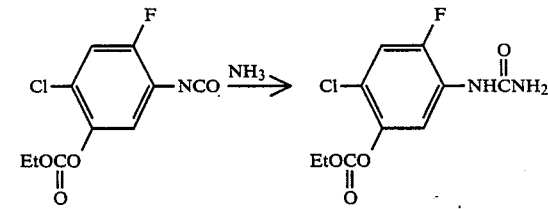

An ammonia gas was introduced into a solution of 2-fluoro-4-chloro-5-ethoxycarbonyloxyphenyl isocyanate (16.7 g, 64 mmol) in benzene (300 ml) while vigorously stirring on cooling in an ice bath. Precipitation of white solid was immediately observed. After thirty minutes the solid deposited was obtained by filtration and sufficiently washed with benzene and dried. This product was identified as 2-fluoro-4-chloro-5-ethoxycarbonyloxyphenyl urea (14.2 g, yield 80%).

$^1$H-NMR (CDCl$_3$-CD$_3$OD, TMS, ppm): δ 1.37 (3H,t,J=7.2 Hz), 4.30 (2H,q,J=7.2 Hz), 7.10 (1H,d,J$_{HF}$=10.2 Hz), 8.07 (1H,d,J=7.2 Hz)

COMPARATIVE EXAMPLE 6

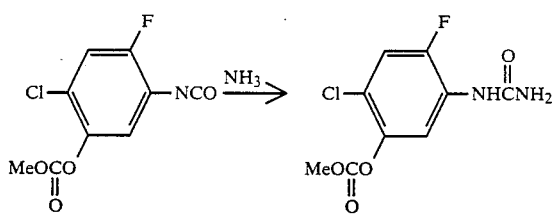

An ammonia gas was introduced into a solution of 2-fluoro-4-chloro-5-methoxycarbonyloxyphenyl isocyanate (12.3 g, 50 mmol) in benzene (100 ml) while vigorously stirring on cooling in an ice bath. Thirty minutes later, the white solid deposited was filtrated and sufficiently washed with benzene and dried. This product was confirmed to be the desired 2-fluoro-4-chloro-5-methoxycarbonyloxyphenyl urea (10.3 g, 78%) by means of spectral analyses.

$^1$H-NMR (DMSO-d$_5$, TMS, ppm): δ 3.87 (3H,s), 5.81 (2H, br s), 7.12 (1H,d,$J_{HF}$=10 Hz), 8.28 (1H,d,$J_{HF}$=7.2 Hz), 8.48 (1H,br s)

COMPARATIVE EXAMPLE 7

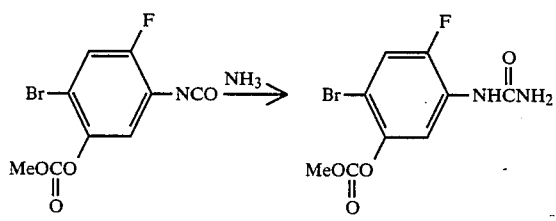

In the same method as that of the Comparative Example 6, 2-fluoro-4-bromo-5-methoxycarbonyloxyphenyl urea (37.7 g, yield 75%) was obtained from 2-fluoro-4-bromo-5-methoxycarbonyloxyphenyl isocyanate (47.7 g, 164 mmol).

$^1$H-NMR (CDCl$_3$-CD$_3$OD, TMS, ppm): δ 3.83 (1H,s), 7.28 (1H,d,$J_{HF}$=10 Hz), 7.99 (1H,d,$J_{HF}$=7.2 Hz)

COMPARATIVE EXAMPLE 8

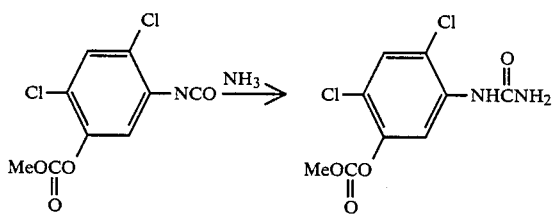

An ammonia gas was introduced while strongly stirring on cooling in an ice bath into a benzene solution (120 ml) of 2,4-dichloro-5-methoxycarbonyloxyphenyl isocyanate (5.04 g, 19.2 mmol) which has been synthesized by the identical method as the Comparative Examples 1 to 4 from 2,4-dichloro-5-methoxycarbonyloxynitrobenzene. Thirty minutes later, a white solid deposited was filtered and sufficiently washed with benzene. This product was confirmed to be the desired 2,4-dichloro-5-methoxycarbonyloxyphenyl urea (4.68 g, yield 88%) by means of spectral analyses.

$^1$H-NMR (CDCl$_3$-DMSO-d$_6$, TMS, ppm): δ 3.88 (3H,s), 6.35 (2H,br), 7.45 (1H,s), 8.20 (1H,br), 8.32 (1H,s)

COMPARATIVE EXAMPLE 9

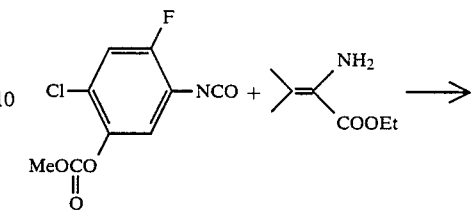

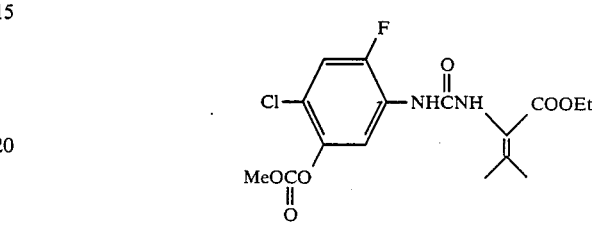

To a benzene solution (100 ml) of 2-fluoro-4-chloro-5-methoxycarbonyloxyphenyl isocyanate (2.45 g, 10 mmol) was added dehydrovaline ethyl ester (1.41 g, 10 mmol), and then the mixture was stirred at room temperature for 10 hours. The solid deposited was filtered off and the filtrate was quenched with a saturated ammonium chloride aqueous solution and extracted with ether (100 ml×3 times). The organic layer was washed with water (50 ml×3 times) and dried over anhydrous magnesium sulfate. After removal of the drying agent, the filtrate was condensed under reduced pressure to give a white solid (3.45 g) of N-(2-fluoro-4-chloro-5-methoxycarbonyloxyphenyl)-N'-(1'-ethoxycarbonyl-2'-methyl-1'-propenyl) urea (yield 92%).

$^1$H-NMR (CD$_3$SOCD$_3$-CDCl$_3$, TMS, ppm): δ 1.27 (3H,t,J=6.9 Hz), 1.87 (3H,s) 2.12 (3H,s), 3.86 (3H,s), 4.20 (2H,q,J=6.9 Hz), 6.74 (1H,br s), 7.05 (1H,d,$J_{HF}$=9.9 Hz), 7.35 (1H,br s), 8.11 (1H,d,$J_{HF}$=7.2 Hz)

IR (KBr disk, cm$^{-1}$): 1770, 1730

COMPARATIVE EXAMPLE 10

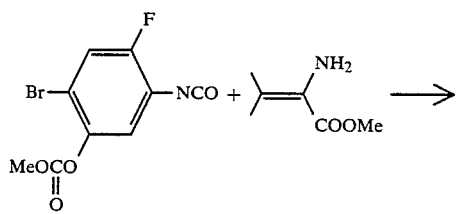

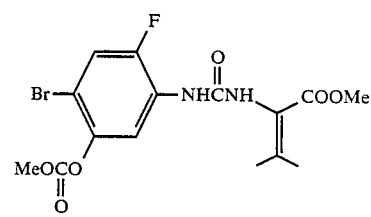

To a benzene solution (100 ml) of 2-fluoro-4-bromo-5-methoxycarbonyloxyphenyl isocyanate (1.28 g, 4.41 mmol) was added dehydrovaline methyl ester (630 mg, 4.88 mmol), and then the mixture was stirred at room temperature for 10 hours. The solid precipitated was removed and the filtrate was quenched with a saturated ammonium chloride aqueous solution and extracted with ether (100 ml×3 times). After washing the organic layer with water (50 ml×3 times) and dried over anhydrous magnesium sulfate. The drying agent was removed and the filtrate was condensed under reduced pressure to precipitate a white solid (483 mg) of N-(2-fluoro-4-bromo-5-methoxycarbonyloxyphenyl)-N-(1'-methoxycarbonyl-2'-methyl-1'-propenyl). The desired white solid was also obtained by filtration after addition of ether to the filtrate. (yield 47%)

$^1$H-NMR (CD$_3$SOCD$_3$-CDCl$_3$, TMS, ppm): δ 1.83 (3H,s), 2.03 (3H,s), 3.67 (3H,s), 3.86 (3H,s), 7.25 (1H,d,J$_{HF}$=10.5 Hz), 7.84 (1H,br s), 8.23 (1H,d,J$_{HF}$=6.9 Hz), 8.58 (1H,br s)

IR (KBr disk, cm$^{-1}$): 1770, 1730

COMPARATIVE EXAMPLE 11

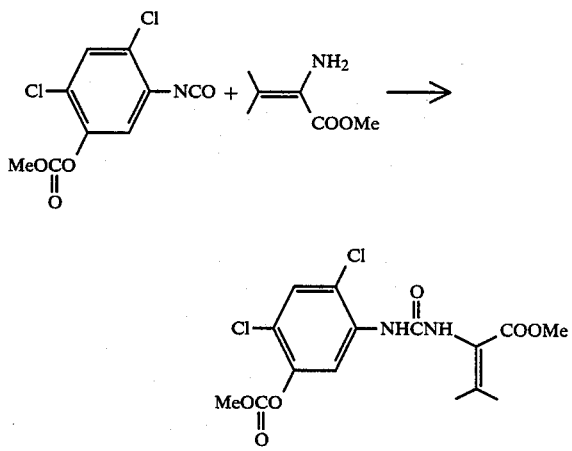

To a benzene solution (100 ml) of 2,4-dichloro-5-methoxycarbonyloxyphenyl isocyanate (1.31 g, 5 mmol) which was been synthesized in the method according to the Comparative Examples 1 to 4 from 2,4-dichloro-5-methoxycarbonyloxynitrobenzene was added dehydrovaline methyl ester (0.65 g, 5 mmol), and the mixture was reacted at room temperature for 7 hours. A small quantity of solid deposited was removed, and the filtrate was washed with an ammonium chloride aqueous solution (500 ml×3 times) and water (50 ml×3 times). After drying, the solvent was removed from the filtrate under reduced pressure, whereby brown oily product (1.35 g) was obtained. After addition of a mixture of ethyl acetate and hexane a white solid deposited was isolated by filtration. This product was identified as N-(2,4-dichloro-5-methoxycarbonyloxyphenyl)-N'-(1'-methoxycarbonyl-2'-methyl-1'-propenyl) urea (1.31 g, yield 58%) by means of spectral analyses.

$^1$H-NMR (CDCl$_3$, TMS, ppm): δ 1.91 (3H,s), 2.17 (3H,s), 3.68 (3H,s), 3.88 (3H,s), 6.63 (1H,br s), 7.31 (1H,br s), 7.35 (1H,s), 8.30 (1H,s)

IR (KBr disk, cm$^{-1}$): 1770, 1725

COMPARATIVE EXAMPLE 12

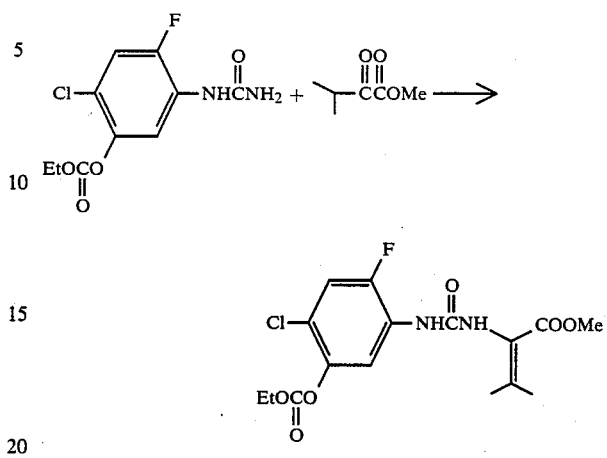

To a benzene solution of 2-fluoro-4-chloro-5-ethoxycarbonyloxyphenyl urea (10.1 g, 36.4 mmol) and a slight excess amount of 2-oxiso-isovaleric acid methyl ester (5.2 g) was added a catalytic amount of p-toluene sulfonic acid (60 mg, 0.35 mmol) and then the mixture was heated at reflux for 4 hours. After completion of the reaction, the resulting mixture was allowed to be cooled and the solid precipitated was filtered off by filtration. The filtrate was then condensed under reduced pressure to give light brown oily product. A light yellow solid (15.5 g) was obtained by recrystallization from ether/penthane. This product was essentially the desired N-(2-fluoro-4-chloro-5-ethoxycarbonyloxyphenyl)-N'-(1'-methoxycarbonyl-2'-methyl-1'-propenyl) urea although it contained a small amount of cyclic product of 3-(2'-fluoro-4'-chloro-5'-ethoxycarbonyloxyphenyl)-5-isopropylidenehydantoin. This mixture was used in the following reaction without isolation or purification.

COMPARATIVE EXAMPLE 13

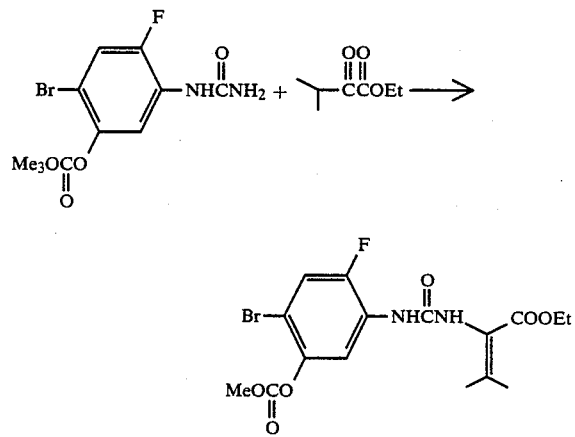

To a toluene (140 ml) solution of 2-fluoro-4-bromo-5-methoxycarbonyloxyphenyl urea (15.2 g, 50 mmol) and 2-oxysoisovalerianic acid ethyl ester (12 ml) in a 200 ml roundbottomed flask equipped with Dean-Stark apparatus was added sodium ethoxide (169 mg) and then the mixture was heated at reflux for 20 hours. After completion of the reaction, the resulting mixture was quenched with a saturated ammonium chloride aqueous solution (100 ml) for acidification and extracted with ether (100 ml×3 times). The organic layer was washed with water, it was dried over anhydrous magnesium sulfate. After removal of the drying agent and condensation of the filtrate under reduced pressure, the light yellow solid (4.6 g) deposited was isolated by filtration. Ether was added to the filtrate, a the light yellow solid precipitated was isolated by filtration. These products were confirmed to be the desired N'-(2-fluoro-4-bromo-5-methoxycarbonyloxyphenyl)-N'-(1'-ethoxycarbonyl-2'-methyl-1'-propenyl) urea by $^1$H-NMR analyses (total yield 28%).

$^1$H-NMR (CDCl$_3$, TMS, ppm): δ 1.26 (3H,t,J=7.2 Hz), 1.83 (3H,s), 2.07 (3H,s), 3.87 (3H,s), 4.19 (2H,q,J=7.2 Hz), 7.08 (1H,br s), 7.18 (1H,d,J$_{HF}$=10.5 Hz), 7.74 (1H,br s), 8.16 (1H,d,J$_{HF}$=7.2 Hz)

COMPARATIVE EXAMPLE 14

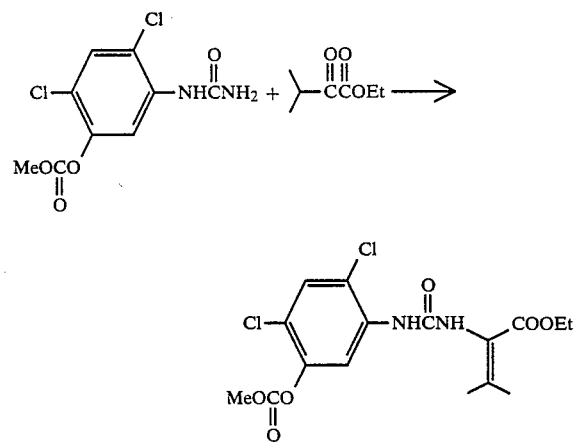

To a benzene (150 ml) solution of 2,4-dichloro-5-methoxycarbonyloxyphenyl urea (10.3 g, 37 mmol) and 2-oxoisovaleri acid ethyl ester (9.0 g) in a round bottom flask equipped with a Dean-Stark apparatus was added p-toluene sulfonic acid (644 g) as a catalyst and then the mixture was heated at reflux for 7 hours. After completion of the reaction, the organic layer was washed with water, and it was dried over anhydrous magnesium sulfate. After removal of the drying agent and condensation of the filtrate under reduced pressure, brown oily product (17.4 g) was obtained. White powder of N-(2,4-dichloro-5-methoxycarbonyloxyphenyl)-N'-(1'-ethoxycarbonyl-2'-methyl-1'-propenyl) urea (7.0 g, yield 47%) was obtained by recrystallization from ethyl acetate/hexane.

$^1$H-NMR (CDCl$_3$, TMS, ppm): δ 1.27 (3H,t,J=7.5 Hz), 1.93 (3H,s), 2.18 (3H,s), 3.88 (3H,s), 4.22 (2H,q,J=7.5 Hz), 6.62 (1H,br s), 7.31 (1H,br s), 7.36 (1H,s), 8.30 (1H,s)

COMPARATIVE EXAMPLE 15

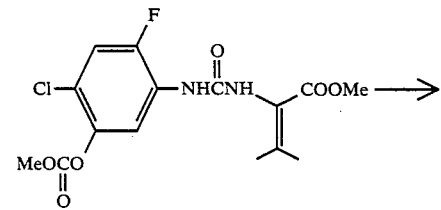

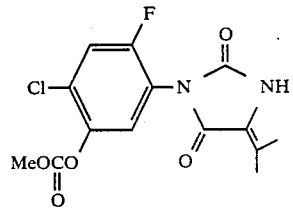

To a toluene (80 ml) solution of N-(2-fluoro-4-chloro-5-methoxycarbonyloxyphenyl)-N'-(1'-ethoxycarbonyl-2'-methyl-1'-propenyl) urea (2.53 g, 6.5 mmol) was added sodium acetate and then the mixture was heated at reflux for 7 hours. After completion of the reaction, ethyl acetate (30 ml) was added. The organic layer was washed with water (20 ml×3 times) and dried over anhydrous magnesium sulfate. After removal of the drying agent and condensation of the filtrate under reduced pressure, a brown oily product was obtained. By addition of ether, the white solid (1.11 g) precipitated was isolated by filtration. After condensation of the mother liquor and addition of ether/hexane mixed solvent, the precipitate (386 mg) was isolated by filtration. These produces were confirmed to be the desired 3-(2'-fluoro-4'-chloro-5'-methoxycarbonyloxyphenyl)-5-isopropylidenehydantoin by $^1$H-NMR analyses (total yield 67%).

$^1$H-NMR (CDCl$_3$, TMS, ppm): δ 1.87 (3H,s), 2.26 (3H,s), 3.91 (3H,s), 7.26 (1H,d,J$_{HF}$=6.9 Hz), 7.31 (1H,d,J$_{HF}$=9.0 Hz), 9.10 (1H,br s)

IR (KBr disk, cm$^{-1}$): 1780, 1730, 1680

COMPARATIVE EXAMPLE 16

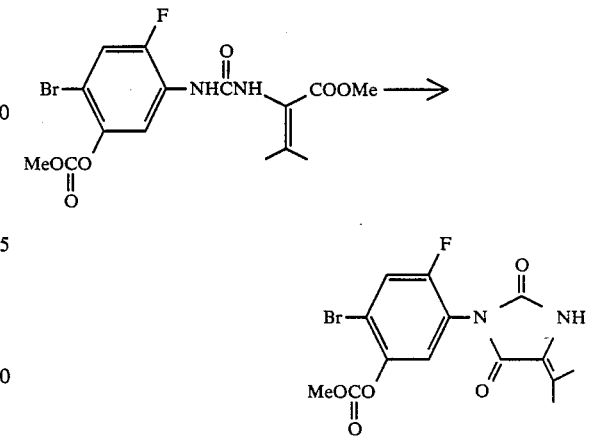

To a toluene (90 ml) solution of N-(2-fluoro-4-bromo-5-methoxycarbonyloxyphenyl)-N'-(1'-methoxycarbonyl-2'-methyl-1'-propenyl) urea (5.66 g, 13.5 mmol) was added sodium acetate (114 mg) and then the mixture was heated at reflux for 3 hours. After cooling the resulting mixture, the solid precipitated was filtered off. The filtrate was washed with water (50 ml×3 times) and dried over anhydrous magnesium sulfate. After removal of the drying agent, the filtrate was condensed under reduced pressure. Ether was added into the residue and the white solid (1.50 g) precipitated was isolated by filtration. After condensation of the filtrate and addition of ether, a white solid (1.94 g) precipitated was isolated by filtration. These products were confirmed to be the desired 3-(2'-fluoro-4'-bromo-5'-methoxycarbonyloxyphenyl)-5-isopropylidenehydantoin by $^1$H-NMR analysis (total yield 68%).

$^1$H-NMR (CDCl$_2$, TMS, ppm): δ 1.86 (3H,s), 2.25 (3H,s), 3.91 (3H,s), 7.29 (1H,d,J$_{HF}$=8.7 Hz), 7.50 (1H,d,J$_{HF}$=9.0 Hz), 9.07 (1H,br s)

IR (KBr disk, cm$^{-1}$): 1780, 1730, 1680

COMPARATIVE EXAMPLE 17

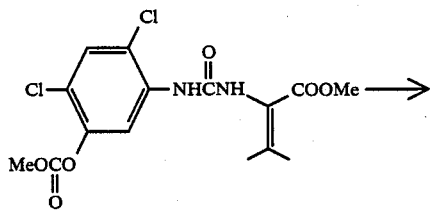

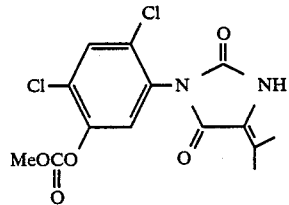

To a benzene (60 ml) solution of N-2,4-dichloro-5-methoxycarbonyloxyphenyl)-N'-(1'-methoxycarbonyl-2'-methyl-1'-propenyl) urea (6.76 g, 17.3 mmol) was added sodium acetate (149 mg) and then the mixture was heated at reflux for 7 hours. After completion of the reaction, the resulting solution was cooled and the solid precipitated was filtered off. The filtrate was washed with water (50 ml×3 times), and was dried over anhydrous magnesium sulfate. After removal of the drying agent, the filtrate was condensed under reduced pressure to give a brown oily product. After addition of chloroform (100 ml), the white solid precipitated of 3-(2',4'-dichloro-5'-methoxycarbonyloxyphenyl)-5-isopropylidenehydantoin (3.97 g, yield 64%) was obtained.

$^1$H-NMR (CDCl$_3$, TMS, ppm): δ 189 (3H,s), 2.28 (3H,s), 3.92 (3H,s), 7.28 (1H,s), 7.63 (1H,s), 8.96 (1H,br s)

IR (KBr disk, cm$^{-1}$): 1780, 1720, 1680

COMPARATIVE EXAMPLE 18

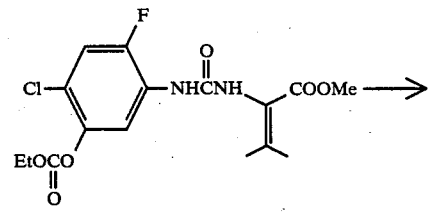

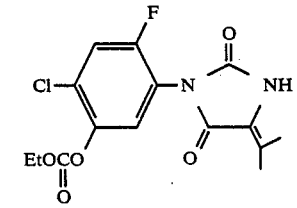

To a benzene (20 ml) solution of N-(2-fluoro-4-chloro-5-ethoxycarbonyloxyphenyl)-N'-(1'-methoxy-2'-methyl-1'-propenyl) urea (1.37 g, 3.5 mmol) was added sodium acetate (300 mg) and heated at reflux for 20 hours. After completion of the reaction, the sodium acetate precipitated was filtered off and the filtrate was condensed under reduced pressure. By recrystallization from ether-penthane, the light yellow solid of 3-(2'-fluoro-4'-chloro-5'-ethoxycarbonyloxyphenyl)-5-isopropylidenehydantoin (1.24 g yield 96%) was obtained.

$^1$H-NMR (CDCl$_3$, TMS, ppm): δ 1.40 (3H,t,J=6.8 Hz), 1.94 (3H,s), 2.30 (3H,s), 4.35 (2H,q,J=6.8 Hz), 7.28 (1H,s), 7.41 (1H,d,J$_{HF}$=2.8 Hz), 8.02 (1H,br s)

COMPARATIVE EXAMPLE 19

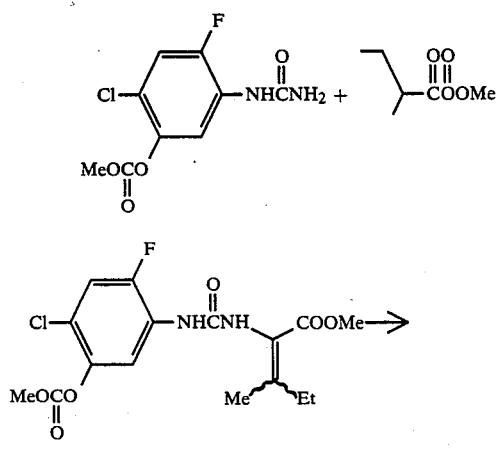

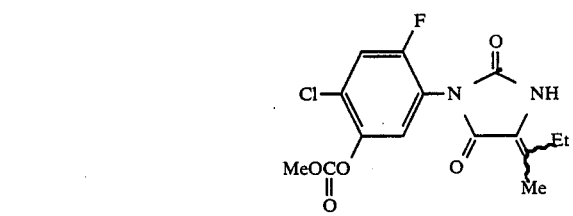

To a benzene (100 ml) solution of N-(2-fluoro-4-chloro-5-methoxycarbonyloxyphenyl) urea (4 g, 15.2 mmol) and 3-methyl-2-oxisovalerianic acid methyl ester (3.4 g, 23.6 mmol) was added p-toluene-sulfonic acid (500 mg) as a catalyst and then the mixture was heated at reflux for 5 hours. After completion of the reaction, the solid precipitated was filtered off. The filtrate was washed with water and was then dried over anhydrous magnesium sulfate. After the drying agent was removed and the solvent was distilled off, ether was added and the white solid precipitated was isolated by filtration. This product was confirmed to be N-(2-fluoro-4-chloro-5-methoxycarbonyloxyphenyl)-N'-(1'-methoxycarbonyl-2'-methyl-1'-butynel) urea by $^1$H-NMR spectrum analysis.

$^1$H-NMR (CDCl$_3$, TMS, ppm): δ 1.03 and 1.12 (total 3H, each t, J=7.5 Hz), 1.87 and 2.10 (total 3H, each s), 2.25 and 2.50 (total 2H, each q, J=7.5 Hz), 3.75 (3H,s), 3.87 (3H,s), 6.48 (1H, br s), 7.08 (1H,d,J$_{HF}$=10.5 Hz), 7.18 (1H, br s), 8.15 and 8.18 (total 1H, each d, J=8.0 Hz)

The resulting N,N'-di-substituted urea was heated at reflux in toluene (100 ml) with the use of p-toluene sulfonic acid (500 mg) as catalyst. After removal of the solid precipitated by filtration, the filtrate was washed with water. After drying it over anhydrous magnesium sulfate, the solvent was removed by distillation. The white solid (2.05 g, yield 38%) of 3-(2'-fluoro-4'-chloro-5-methoxycarbonyloxyphenyl)-5-(2'-butylidene)hydantoin was obtained by recrystallization from ether/hexane.

1H-NMR (CDCl3, TMS, ppm): δ 1.07 and 1.18 (total 3H, each t, J=7.5 Hz), 1.65 and 1.87 (total 3H, each s), 2.17 and 2.75 (total 2H, each q, J=7.5 Hz), 3.98 (3H,s), 7.25 (1H,d,$J_{HF}$=3 Hz), 7.35 (1H,d,$J_{HF}$=4.5 Hz), 8.78 (1H,m)

COMPARATIVE EXAMPLE 20

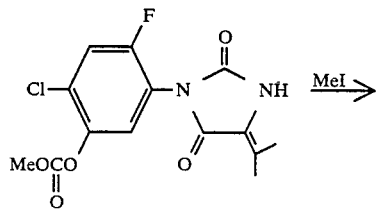

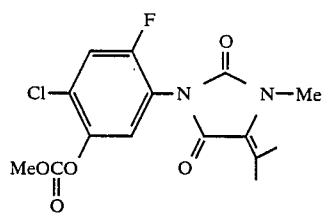

To a N,N-dimethylformamide solution (200 ml) of 3-(2'-fluoro-4'-chloro-5'-methoxycarbonyloxyphenyl)-5-isopropylidenehydantoin (8.1 g, 22.7 mmol) was added potassium carbonate (16.9 g) and methyl iodide (15 ml) and then the mixture was stirred at 40° C. for 4 hours. After completion of the reaction, the resulting mixture was quenched with a saturated ammonium chloride aqueous solution and extracted with ether (100 ml×3 times). The organic layer was washed with water (50 ml×3 times) and dried over anhydrous magnesium sulfate. After removal of the drying agent by filtration a brown oily product (6.5 g, yield 78%) was obtained by condensation of the filtrate under reduced pressure. This product was confirmed to be 1-methyl-3-(2'-fluoro-4'-chloro-5'-methoxycarbonyloxyphenyl)-5-isopropylidenehydantoin by spectral analyses.

1H-NMR (CDCl3, TMS, ppm): δ 2.17 (3H,s), 2.34 (3H,s), 3.42 (3H,s), 3.85 (3H,s), 7.27 (1H,d,$J_{HF}$=2.9 Hz), 7.40 (1H,d,$J_{HF}$=4.5 Hz)

COMPARATIVE EXAMPLE 21

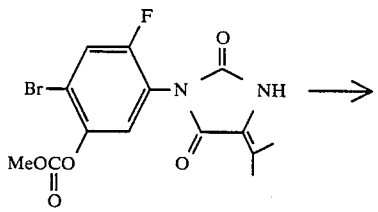

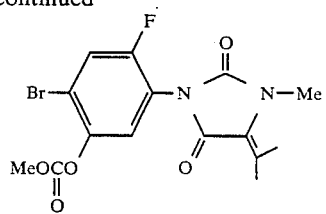

To a N,N-dimethylformamide solution (70 ml) of 3-(2'-fluoro-4'-bromo-5'-methoxycarbonyloxyphenyl)5-isopropylidene-hydantoin (1.5 g, 3.7 mmol) was added potassium carbonate (2.51 g) and methyl iodide (3.4 ml) and then the mixture was stirred at 50° C. for 2 hours. After completion of the reaction, the resulting mixture was quenched with 1N-hydrochloric acid and extracted with ether (40 ml×3 times). The organic layer was washed with water (20 ml×3 times), and dried over anhydrous magnesium sulfate. After removal of the drying agent by filtration a colorless transparent oily product (1.27 g, yield 81%) was obtained by condensation of the filtrate under reduced pressure. This product was confirmed to be 1-methyl-3-(2'-fluoro-4'-bromo-5'-methoxycarbonyloxyphenyl)-5-isopropylidenehydantoin by spectral analyses.

1H-NMR (CDCl3, TMS, ppm): δ 2.17 (3H,s), 2.34 (3H,s), 3.44 (3H,s), 3.83 (3H,s), 6.78 (1H,d,$J_{HF}$=6 Hz), 7.41 (1H,d,$J_{HF}$=9 Hz)

COMPARATIVE EXAMPLE 22

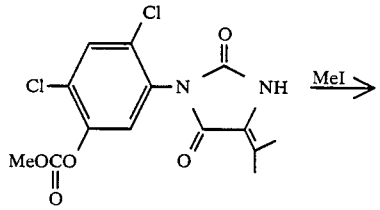

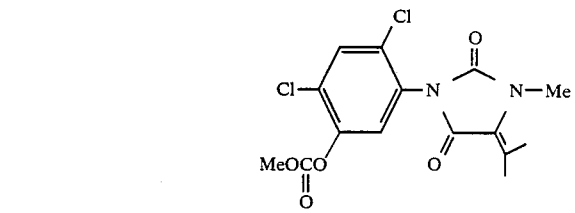

To a N,N-dimethylformamide solution (30 ml) of 3-(2',4'-dichloro-5'-methoxycarbonyloxyphenyl)-5-isopropylidenehydantoin (602 mg, 1.68 mmol) was added potassium carbonate (1.2 g) and methyl iodide (2.5 g) and then the mixture was stirred at 50° C. for 2 hours. After completion of the reaction, the resulting mixture was quenched with 1N-hydrochloric acid and extracted with ether (20 ml×3 times). The organic layer was washed with water (10 ml×3 times), and dried over anhydrous magnesium sulfate. After removal of the drying agent by filtration a colorless transparent oily product (590 mg, yield 91%) was obtained by condensation of the filtrate under reduced pressure. This product was confirmed to be 1-methyl-3-(2',4'-dichloro-5=-methoxycarbonyloxyphenyl)-5-isopropylidenehydantoin by spectral analyses.

1H-NMR (CDCl3, TMS, ppm): δ 2.16 (3H,s), 2.33 (3H,s), 3.39 (3H,s), 3.88 (3H,s), 7.28 (1H,s), 7.60 (1H,s)

TABLE 2

Physical Properties of Hydantoin Derivatives

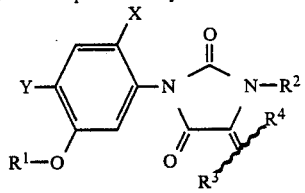

| Compound No. | m.p. (°C.) | Molecular formula | C (%) Found | C (%) Calcd. | H (%) Found | H (%) Calcd. | N (%) Found | N (%) Calcd. | IR spectrum (cm$^{-1}$) |
|---|---|---|---|---|---|---|---|---|---|
| 1 | 244–245 | $C_{12}H_{10}Cl_2N_2O_3$ | 47.63 | 47.86 | 3.51 | 3.35 | 9.35 | 9.30 | 1750, 1710 |
| 2 | 207–209 | $C_{12}H_{10}FClN_2O_3$ | 50.44 | 50.63 | 3.61 | 3.54 | 9.80 | 9.84 | 1780, 1720 |
| 3 | 206–206.5 | $C_{12}H_{10}BrFN_2O_3$ | 43.85 | 43.79 | 3.18 | 3.06 | 8.19 | 8.51 | 1770, 1710 |
| 4 | 96–97 | $C_{13}H_{12}BrFN_2O_3$ | 45.56 | 45.50 | 3.36 | 3.52 | 8.37 | 8.16 | 1780, 1720 |
| 5 | 85–87 | $C_{15}H_{16}Cl_2N_2O_3$ | 52.00 | 52.49 | 4.73 | 4.70 | 8.05 | 8.16 | 1770, 1720 |
| 6 | 134–137 | $C_{15}H_{12}ClFN_2O_3$ | 55.53 | 55.83 | 3.83 | 3.75 | 8.65 | 8.68 | 1720, 1640 |
| 7 | 121–122 | $C_{14}H_{14}Cl_2N_2O_3$ | 51.11 | 51.08 | 4.30 | 4.29 | 8.38 | 8.51 | 1760, 1710 |
| 8 | 114–117 | $C_{16}H_{14}Cl_2N_2O_3$ | 54.27 | 54.41 | 4.02 | 4.00 | 7.05 | 7.93 | 1770, 1720 |
| 9 | oil | $C_{16}H_{18}Cl_2N_2O_3$ | 53.73 | 53.80 | 4.79 | 5.08 | 7.76 | 7.84 | 1790, 1750 |
| 10 | 123–124 | $C_{14}H_{14}ClFN_2O_3$ | 53.30 | 53.77 | 4.44 | 4.51 | 8.81 | 8.96 | 1770, 1720 |
| 11 | oil | $C_{16}H_{18}ClFN_2O_3$ | 56.44 | 56.39 | 5.53 | 5.32 | 8.36 | 8.22 | 1790, 1750 |
| 12 | 152–153 | $C_{16}H_{14}ClFN_2O_3$ | 56.54 | 57.07 | 4.11 | 4.19 | 8.20 | 8.32 | 1770, 1720 |
| 13 | 106–109 | $C_{16}H_{15}Cl_2FN_2O_3$ | 50.84 | 51.49 | 3.94 | 4.05 | 7.39 | 7.51 | 1770, 1740 |
| 14 | 94–99 | $C_{16}H_{15}Cl_2FN_2O_3$ | 51.50 | 51.49 | 4.37 | 4.05 | 7.13 | 7.51 | 1770, 1730 |
| 15 | 107–109 | $C_{17}H_{16}ClFN_2O_3$ | 58.18 | 58.21 | 4.43 | 4.60 | 7.76 | 7.99 | 1770, 1730 |
| 16 | 70–72 | $C_{21}H_{24}ClFN_2O_3$ | 61.81 | 61.99 | 6.16 | 5.95 | 6.57 | 6.88 | 1760, 1710 |
| 17 | 109–111 | $C_{14}H_{14}BrFN_2O_3$ | 47.03 | 47.08 | 3.99 | 3.95 | 7.76 | 7.84 | 1770, 1720 |
| 18 | oil | $C_{16}H_{18}BrFN_2O_3$ | 49.08 | 49.89 | 4.70 | 4.71 | 7.13 | 7.27 | 1770, 1725 |
| 19 | 142–144 | $C_{16}H_{14}BrFN_2O_3$ | 50.12 | 50.41 | 3.63 | 3.70 | 7.33 | 7.35 | 1770, 1730 |
| 20 | oil | $C_{18}H_{22}ClFN_2O_3$ | 58.76 | 58.62 | 5.62 | 6.01 | 7.88 | 7.60 | 1770, 1720 |
| 21 | 106–109 | $C_{16}H_{16}ClFN_2O_3$ | 56.59 | 56.73 | 4.71 | 4.76 | 7.99 | 8.27 | 1780, 1720 |
| 22 | oil | $C_{17}H_{18}ClFN_2O_3$ | 57.88 | 57.88 | 5.35 | 5.14 | 7.68 | 7.94 | 1770, 1720 |
| 23 | 124–127 | $C_{16}H_{16}ClFN_2O_3$ | 56.89 | 56.73 | 4.83 | 4.76 | 8.10 | 8.27 | 1760, 1720 |
| 24 | 176–177 | $C_{18}H_{20}ClFN_2O_3$ | 58.87 | 58.94 | 5.46 | 5.50 | 7.53 | 7.64 | 1760, 1720 |
| 25 | 162–163 | $C_{19}H_{22}Cl_2N_2O_3$ | 57.46 | 57.44 | 5.48 | 5.58 | 7.13 | 7.05 | 1760, 1720 |
| 26 | 109–111 | $C_{18}H_{16}Cl_4N_2O_3$ | 48.15 | 48.03 | 3.85 | 3.58 | 6.35 | 6.22 | 1770, 1720 |
| 27 | oil | $C_{18}H_{18}Cl_2N_2O_3$ | 56.93 | 56.71 | 4.85 | 4.76 | 7.41 | 7.35 | 1770, 1720 |
| 28 | 131–133 | $C_{18}H_{14}Cl_2N_2O_3$ | 57.45 | 57.31 | 3.65 | 3.74 | 7.13 | 7.43 | 1780, 1730 |
| 29 | oil | $C_{20}H_{22}ClFN_2O_3$ | 61.54 | 61.15 | 5.85 | 5.64 | 7.54 | 7.13 | 1760, 1720 |
| 30 | oil | $C_{18}H_{18}BrFN_2O_3$ | 52.51 | 52.83 | 4.31 | 4.43 | 6.53 | 6.85 | 1770, 1725 |
| 31 | oil | $C_{18}H_{16}BrCl_2FN_2O_3$ | 45.53 | 45.22 | 3.48 | 3.37 | 5.98 | 5.86 | 1770, 1720 |
| 32 | oil | $C_{18}H_{16}BrCl_2FN_2O_3$ | 45.83 | 45.22 | 3.52 | 3.37 | 5.89 | 5.86 | 1770, 1720 |
| 33 | 156–157 | $C_{18}H_{14}BrFN_2O_3$ | 53.38 | 53.35 | 3.43 | 3.48 | 6.87 | 6.91 | 1765, 1720 |
| 34 | oil | $C_{15}H_{16}ClFN_2O_3$ | 55.38 | 55.14 | 4.73 | 4.94 | 8.42 | 8.57 | 1760, 1720 |
| 35 | 159–164 | $C_{13}H_{12}ClFN_2O_3$ | 52.25 | 52.27 | 4.13 | 4.05 | 9.15 | 9.38 | 1765, 1710 |
| 36 | 56–62 | $C_{16}H_{14}BrFN_2O_3$ | 50.53 | 50.41 | 3.81 | 3.70 | 7.24 | 7.35 | 1775, 1725 |

TABLE 3

NMR Spectral Data of Hydantoin Derivatives

| Compound No. | $^1$H—NMR spectral data (CDCl$_3$, TMS, δ ppm) |
|---|---|
| 1 | 1.94(3H,s), 2.25(3H,s), 6.93(1H,s), 7.42(1H,s), 10.07(1H, br s), 10.18(1H,br s). (in CD$_3$SOCD$_3$—CDCl$_3$) |
| 2 | 1.95(3H,s), 2.30(3H,s), 6.83(1H,d,J$_{HF}$=6.6Hz), 7.20(1H,d,J$_{HF}$=9.0Hz). (in CD$_3$OD—CDCl$_3$) |
| 3 | 1.93(3H,s), 2.24(3H,s), 6.90(1H,d,J$_{HF}$=6.6Hz), 7.31(1H,d,J$_{HF}$=9.0Hz), 9.95(1H,br s), 10.13(1H,br s). (in CD$_3$SOCD$_3$—CDCl$_3$) |
| 4 | 2.14(3H,s), 2.31(3H,s), 3.40(3H,s), 6.75(1H,d,J$_{HF}$=6.6Hz),7.03(1H,br s), 7.29(1H,d,J$_{HF}$=9.0Hz). (in CD$_3$OD) |
| 5 | 1.35(6H,d,J=6.0Hz), 1.84(3H,s), 1.92(3H,s), 4.48(1H,sep,J=6.0Hz), 6.89(1H,s), 7.51(1H,s), 9.39(1H,br s) |
| 6 | 1.94(3H,s), 2.26(3H,s), 2.65(1H,t,J=2.1Hz), 4.73(2H,d,J=2.1Hz), 7.04(1H,d,J$_{HF}$=6.9Hz), 7.19(1H,d,J$_{HF}$=4.2Hz), 10.04(1H,br s) |
| 7 | 2.20(3H,s), 2.37(3H,s), 3.46(3H,s), 3.87(3H,s), 6.83(1H,s), 7.52(1H,s) |
| 8 | 2.16(3H,s), 2.34(3H,s), 2.58(1H,t,J=1.8Hz), 3.43(3H,s), 4.72(2H,d,J=1.8Hz), 6.99(1H,s), 7.52(1H,s) |
| 9 | 1.36(6H,d,J=6.0Hz), 2.18(3H,s), 2.35(3H,s), 3.44(3H,s), 4.81(1H,sep,J=6.0Hz), 6.83(1H,s), 7.49(1H,s) |
| 10 | 2.21(3H,s), 2.37(3H,s), 3.46(3H,s), 3.87(3H,s), 6.83(1H,d,J$_{HF}$=6.2Hz), 7.29(1H,d,J$_{HF}$=9.0Hz) |
| 11 | 1.36(6H,d,J=6.0Hz), 2.16(3H,s), 2.43(3H,s), 3.42(3H,s), 4.41(1H,sep,J=6.0Hz), 6.84(1H,d,J$_{HF}$=6.3Hz), 7.23(1H,d,J$_{HF}$=9.0Hz) |
| 12 | 2.17(3H,s), 2.33(3H,s), 2.47(1H,t,J=2.4Hz), 3.40(3H,s), 4.66(2H,d,J=2.4Hz), 6.90(1H,d,J$_{HF}$=6.0Hz), 7.18(1H,d,J$_{HF}$=8.8Hz) |
| 13 | 2.17(3H,s), 2.34(3H,s), 3.43(3H,s), 4.55(2H,br s), 5.39–5.73(2H,m), 6.81(1H,d,J$_{HF}$=6.3Hz), 7.26(1H,d,J$_{HF}$9.0Hz) |

TABLE 3-continued
NMR Spectral Data of Hydantoin Derivatives

| Compound No. | $^1$H—NMR spectral data (CDCl$_3$, TMS, δ ppm) |
|---|---|
| 14 | 2.31(3H,s), 2.33(3H,s), 3.40(3H,s), 4.50(1H,d,J=6.0Hz), 4.74(1H,m), 5.96–6.37(2H,m), 6.91(1H,d,J$_{HF}$=6.0Hz), 7.04(1H,d,J$_{HF}$=6.6Hz) |
| 15 | 1.27(3H,t,J=7.05Hz), 2.13(3H,s), 2.36(3H,s), 2.56(1H,t,J=2.1Hz), 3.92(3H,q,J=7.05Hz), 4.70(2H,d,J=2.1Hz), 6.99(1H,J$_{HF}$=6.0Hz), 6.91(1H,d,J$_{HF}$=9.0Hz) |
| 16 | 0.89(3H,br t), 1.31(8H,m), 2.11(3H,s), 2.35(3H,s), 2.54(1H,t,J=1.8Hz), 3.84(2H,t,J=6.2Hz), 4.70(2H,d,J=1.8Hz), 6.99(1H,d,J$_{HF}$=6.2Hz), 7.24(1H,d,J$_{HF}$=9.0Hz) |
| 17 | 2.17(3H,s), 2.34(3H,s), 3.44(3H,s), 3.83(3H,s), 6.78(1H,d,J$_{HF}$=6.0Hz), 7.41(1H,d,J$_{HF}$=9.0Hz) |
| 18 | 1.37(6H,d,J=6.0Hz), 2.18(3H,s), 2.35(3H,s), 3.44(3H,s), 4.45(1H,sep,J=6.0Hz), 6.84(1H,d,J$_{HF}$=6.0Hz), 7.42(1H,d,J$_{HF}$=9.0Hz) |
| 19 | 2.17(3H,s), 2.35(3H,s), 2.57(1H,t,J=2.1Hz), 3.44(3H,s), 4.71(2H,d,J=2.1Hz), 6.99(1H,d,J$_{HF}$=6.3Hz), 7.44(1H,d,J$_{HF}$=9.0Hz) |
| 20 | 1.02(6H,d,J=6.0Hz), 1.53(6H,d,J=6.6Hz), 2.08(3H,s), 2.33(3H,s), 4.13(1H,sep,J=6.6Hz), 4.43(1H,sep,J=6.0Hz), 6.82(1H,d,J$_{HF}$=6.3Hz), 7.20(1H,d,J$_{HF}$=9.0Hz) |
| 21 | 2.18(3H,s), 2.36(3H,s), 3.45(3H,s), 4.53(2H,m), 5.18–5.53(2H,m), 5.81–6.30(1H,m), 6.83(1H,d,J$_{HF}$=6.6Hz), 7.24(1H,d,J$_{HF}$=9.0Hz) |
| 22 | 1.83(3H,dd,J=0.9 and 1.5Hz), 2.20(3H,s), 2.37(3H,s), 3.46(3H,s), 4.45(2H,dd,J=1.0 and 1.5Hz), 5.01(1H,qt d,J=1.5, 1.0 and 1.5Hz), 5.13(1H,qt d, J=0.9, 1.5 and 1.5Hz), 6.84(1H,d,J$_{HF}$6.4Hz), 7.28(1H,d,J$_{HF}$=9.0Hz) |
| 23 | 0.92(2H,m), 1.21(2H,m), 2.18(3H,s), 2.35(3H,s), 2.83(1H,m), 3.44(3H,s), 6.80(1H,d,J$_{HF}$=6.3Hz), 7.14(1H,d,J$_{HF}$=9.0Hz) |
| 24 | 1.36–2.06(8H,br), 2.17(3H,s), 2.36(3H,s), 3.43(3H,s), 4.70(1H,m), 6.85(1H,d,J$_{HF}$=6.3Hz), 7.24(1H,d,J$_{HF}$=9.0Hz) |
| 25 | 1.23–1.88(10H,br), 2.19(3H,s), 2.36(3H,s), 3.43(3H,s), 4.20(1H,m), 6.80(1H,s), 7.47(1H,s) |
| 26 (E-Z)[1] | 2.14(3H,s), 2.39(3H,s), 4.52(2H,dd,J=5.5 and 1.6Hz), 4.82(2H,dd,J=5.7 and 1.9Hz), 6.03(1H,dt, J=13.4 and 5.5Hz), 6.08(1H,dt,J=7.3 and 5.7Hz), 6.25(1H,dt,J=13.4 and 1.6Hz), 6.29(1H,dt,J=7.3 and 1.9Hz), 6.86(1H,s), 7.55(1H,s) |
| 26 (Z-E)[2] | 2.12(3H,s), 2.37(3H,s), 4.54(2H,dd,J=5.8 and 1.6Hz), 4.71(2H,dd,J=5.4 and 2.1Hz), 5.91(1H,dt,J=7.3 and 5.4Hz), 6.16(1H,dt,J=13.3 and 5.8Hz), 6.24(1H,dt,J=7.3 and 2.1Hz), 6.45(1H,dt,J=13.3 and 1.6Hz), 6.83(1H,s), 7.56(1H,s) |
| (E-E)[3] | 2.14(3H,s), 2.38(3H,s), 4.52(2H,dd,J=5.5 and 1.5Hz), 4.56(2H,dd,J=5.8 4.64(2H,t,J=1.5Hz), 6.03(1H,dt,J=13.4 and 5.5Hz), 6.17(1H,dt,J=13.4 and 5.8Hz), 6.25(1H,dt,J=13.4 and 1.5Hz), 6.46(1H,dt,J=13.4 and 1.5Hz), 6.83(1H,s), 7.56(1H,s) |
| 27 | 1.36(6H,d,J=6.0Hz), 2.25(3H,s), 2.35–2.39(4H,m), 4.48(1H,sep,J=6.0Hz), 4.64(2H,m), 6.87(1H,s), 7.51(1H,s) |
| 28 | 2.29(3H,s), 2.39(1H,dd,J=2.4 and 2.5Hz), 2.41(3H,s), 2.59(1H,t,J=2.4Hz), 4.60(1H,dd,J=18.2 and 2.4Hz), 4.75(1H,dd,J=18.2 and 2.5 Hz), 4.76(2H,d,J=2.4Hz), 7.02(1H,s), 7.56(1H,s) |
| 29 | 1.78(3H,s), 1.84(3H,s), 2.06(3H,s), 2.36(3H,s), 4.37(2H,s), 4.46(2H,m), 4.82(1H,m), 5.00(1H,m), 5.01(1H,m), 5.14(1H,m), 6.87(2H,d,J$_{HF}$=6.4Hz), 7.29(1H,d,J$_{HF}$=9.0Hz) |
| 30 | 1.36(6H,d,J=6.0Hz), 2.24(3H,s), 2.36(1H,t,J=2.1Hz), 2.37(3H,s), 4.44(1H,sep,J=6.0Hz), 4.62(2H,d,J=2.1Hz), 6.84(1H,d,J$_{HF}$=6.0Hz), 7.41(1H,d,J$_{HF}$=9.0Hz) |
| 31 | 2.07(3H,s), 2.36(3H,s), 4.57(4H,br s), 5.33(1H,m), 5.43(2H,m), 5.66(1H,m), 6.82(1H,d,J$_{HF}$=6.6Hz), 7.43(1H,d,J$_{HF}$=9.0Hz) |
| 32 (E-E)[4] | 2.11(3H,s), 2.36(3H,s), 4.46(2H,dd,J=5.2 and 2.0Hz), 4.50(2H,dd,J=4.8 and 1.2Hz), 5.97(1H,dt,J=13.4 and 4.8Hz), 6.11(1H,dt,J=13.4 and 5.2Hz), 6.25(1H,dt,J=13.4 and 2.0Hz), 6.44(1H,dt,J=13.4 and 1.2Hz), 6.80(1H,d,J$_{HF}$=6.0Hz), 7.44(1H,d,J$_{HF}$=9.0Hz) |
| (E-Z, Z-E)[5] | 2.10(6H,s), 2.34(6H,s), 4.44–4.80(8H,m), 5.74–6.52(8H,m), 6.79(1H,d,J$_{HF}$=6.0Hz), 6.81(1H,d,J$_{HF}$=6.0Hz) |
| 33 | 2.27(3H,s), 2.36(1H,t,J=2.1Hz), 2.39(3H,s), 2.56(1H,t,J=2.1Hz), 4.64(2H,t,J=2.1Hz), 4.73(2H,d,J=2.1Hz), 7.00(1H,d,J$_{HF}$=6.0Hz), 7.45(1H,d,J$_{HF}$=9.0Hz) |
| 34[6] | 1.10 and 1.19(total 3H, each t, J=8.1Hz), 2.15 and 2.31(total 3H, each s), 2.48 and 2.80(total 2H, each q, J=8.1Hz), 3.42(3H,s), 3.84(3H,s), 6.83(1H,d,J$_{HF}$=6.3Hz), 7.26(1H,d,J$_{HF}$=9.0Hz) |
| 35[6] | 1.05 and 1.07(total 3H, each t, J=8.0Hz), 1.82 and 2.22(total 3H, each s), 2.13 and 2.72(total 2H, each q, J=8.0Hz), 6.87(1H,d,J$_{HF}$=6.6Hz), 7.13(1H,d,J$_{HF}$=9.0Hz), 8.93(1H,s), 8.97(1H,s) |
| 36[6] | 1.13(6H,d,J=7.0Hz), 2.53(1H,t,J=2.5Hz), 2.60(1H,m), 4.70(2H,d,J=2.5Hz), 5.90(1H,d,J=9.0Hz), 6.98(1H,d,J$_{HF}$=6.0Hz), 7.44(1H,d,J=8.0Hz), |

TABLE 3-continued
NMR Spectral Data of Hydantoin Derivatives
Compound No. $^1$H—NMR spectral data (CDCl$_3$, TMS, δ ppm)

8.01(1H,br s)

$^1$1-(3'-chloro-2'(E)-propenyl-3-{2'',4''-dichloro-5''-(3'''-chloro-2'''(E)-propenyloxy)phenyl}-5-isopropylidenehydantoin
$^2$1-(3'-chloro-2'(Z)-propenyl-3-{2'',4''-dichloro-5''-(3'''-chloro-2'''(E)-propenyloxy)phenyl}-5-isopropylidenehydantoin
$^3$1-(3'-chloro-2'(E)-propenyl-3-{2'',4''-dichloro-5''-(3'''-chloro-2'''(Z)-propenyloxy)phenyl}-5-isopropylidenehydantoin
$^4$1-(3'-chloro-2'(E)-propenyl-3-{2''-fluoro-4''-bromo-5''-(3'''-chloro-2'''(E)-propenyloxy)phenyl} -5-isopropylidenehydantoin
$^5$The mixture of 1-(3'-chloro-2'(E)-propenyl-3-{2''-fluoro-4''-bromo-5''-(3'''-chloro-2'''(Z)-propenyloxy)phenyl}-5-isopropylidenehydantoin and 1-(3'-chloro-2'(Z)-propenyl-3-}2''-fluoro-4''-bromo-5''-(3'''-chloro-2'''(Z)-propenyloxy)phenyl}-5-isopropylidenehydantoin
$^6$The compounds asterisked are mixtures of cis and trans isomers with respect to the stereochemistry of the double bonds at the 5-positions of the hydantoin rings The compound thus obtained has the superior herbicidal activities as described above.

The compounds can be used solely as a herbicide, or can be used in combination with one or more adjuvants. Conventional adjuvants are exemplified by various carriers, diluents, solvents, surface active agents, stabilizers, which are preferably mixed and formulated in by normal method into a wettable powder, emulsible concentrate, dust formulation, and granules or other form.

The solvent that employed as an adjuvant for the herbicide according to the present invention is preferably water, alcohols, ketones, ethers, aliphatic or aromatic hydrocarbons, halogenated hydrocarbons, acid amides, esters, nitriles or the like. Mixture of one or more of them may be used. As the diluent, clays such as kaoline, bentonite and so forth, talcs such as talc and pyrophyllite and so forth, mineral dust of an oxide of diatomaceous earth and white carbon and so forth, or a vegetative dust such as soybean powder, CMC and so forth may suitably be used, either alone or as a mixture of more than one thereof.

Furthermore, the surface active agent may be a spreading agent, dispersant, emulsifier or penetrant. This surface active agent ay be exemplified by nonionic surface active agents, cationic surface active agents, anionic surface active agents and amphoteric surface active agents and so forth. Such surface active agents may be used alone o, as a mixture of more than one thereof.

Preferable methods of using the herbicide include soil treatment, treatment and application to stem and leaf portions, and so forth. It is particularly effective when used before germination or before the plumule stage.

The herbicide according to the present invention can be used simultaneously or in a mixture with other active ingredients which do not deteriorate the herbicidal activity of the effective ingredient of the herbicide according to the present invention, for example, herbicides, pesticides, fungicides and growth regulators and so forth.

In order to further explain the present invention, the examples of formulation and the results of an experiment on the herbicidal activity of the herbicide according to the present invention will now be described. The object of the description of the following embodiments is not to limit the present invention. It is also to be noted that the unit parts used in the description refer to weight basis.

FORMULATION EXAMPLE 1 (EMULSION)

The compound according to the present invention (20 parts) was mixed equally with, 35 parts xylene, 40 parts cyclohexane, and 5 parts Sobol 900A (prepared by Toho Chemical Industry Co., Ltd.) for the purpose of formulation.

FORMULATION EXAMPLE 2 (WETTABLE AGENT)

The compound according to the present invention (50 parts) was mixed with 25 parts diatomaceous earth, 22 parts clay and 3 parts Runox R100C (Toho Chemical Industry Co., Ltd.) and the mixture was equally crushed to prepare a wettable agent.

FORMULATION EXAMPLE 3 (DUST FORMULATION)

The compound according to the present invention (5 parts), was mixed and crushed equally with 35 parts bentonite, 55 parts talc, 5 parts sodium lignin sulfonata and then kneaded with water for dust formulation by employment of an extruding granulator, and finally dried and brought into whole grain.

EXPERIMENTAL EXAMPLE 1 (EFFECT ON WEEDS IN PADDY FIELDS)

The soil of a paddy field was filled in Wagner pots having an area of 1/5,000 are in which the seeds of *Echinochloa crus-galli, Monochoria vaginalis, Ammannia multiflora* and paddy seedings (grade: Nihonbare) of a 3-4 leaf time were respectively sown or transplanted and kept in a state filled with water. After 5 days, each of the water surface was treated with water. After 5 days, each of the water surface was treated with given amounts of each herbicide of the present invention which was formed into granules in accordance with Preparation Example 3 so that the effective ingredient thereof became 20, 10 and 5 g per are, respectively. After 30 days from the treatment with the granules, the weed-killing effect on the plants to be examined and the phytotoxicity of the paddy were examined on the basis of the following criteria and the results given in Table 4 were obtained.

| Degree of weed-killing | Criteria<br>Percentage of remaining weeds (%) |
|---|---|
| 0 | 81–100 |
| 1 | 61–80 |
| 2 | 41–60 |
| 3 | 21–40 |
| 4 | 6–20 |
| 5 | 0–5 |
| Phytotoxicity | |
| − | No damage |
| + | Slight damage |
| ++ | Small damage |
| +++ | Medium damage |

| | -continued | | |
|---|---|---|---|
| | Criteria | ++++ | Heavy damage |
| Degree of weed-killing | Percentage of remaining weeds (%) | x | Dead |

TABLE 4

Effects on Weeds in Paddy Fields

| Test Compound No. | Dose (g/a) | Degree of Weed Killing | | | Phytotoxicity Rice |
|---|---|---|---|---|---|
| | | Echirochloa crus-gall | Monochoria vaginalis | Ammania multiflora | |
| 1 | 20 | 2 | 5 | 4 | — |
| | 10 | 1 | 3 | 3 | — |
| | 5 | 0 | 2 | 1 | — |
| 2 | 20 | 2 | 5 | 4 | — |
| | 10 | 1 | 4 | 3 | — |
| | 5 | 0 | 2 | 1 | — |
| 3 | 20 | 3 | 5 | 5 | + |
| | 10 | 2 | 4 | 4 | — |
| | 5 | 1 | 3 | 2 | — |
| 6 | 20 | 5 | 5 | 5 | ++ |
| | 10 | 5 | 5 | 5 | + |
| | 5 | 5 | 5 | 5 | — |
| 7 | 20 | 5 | 5 | 5 | ++ |
| | 10 | 5 | 5 | 5 | + |
| | 5 | 4 | 5 | 5 | — |
| 8 | 20 | 5 | 5 | 5 | ++ |
| | 10 | 5 | 5 | 5 | + |
| | 5 | 5 | 5 | 5 | — |
| 9 | 20 | 5 | 5 | 5 | + |
| | 10 | 5 | 5 | 5 | — |
| | 5 | 4 | 5 | 5 | — |
| 10 | 20 | 5 | 5 | 5 | ++ |
| | 10 | 5 | 5 | 5 | + |
| | 5 | 5 | 5 | 5 | — |
| 11 | 20 | 5 | 5 | 5 | + |
| | 10 | 4 | 5 | 5 | — |
| | 5 | 3 | 5 | 5 | — |
| 12 | 20 | 5 | 5 | 5 | +++ |
| | 10 | 5 | 5 | 5 | ++ |
| | 5 | 5 | 5 | 5 | + |
| 13 | 20 | 5 | 5 | 5 | + |
| | 10 | 4 | 5 | 5 | — |
| | 5 | 2 | 5 | 4 | — |
| 14 | 20 | 5 | 5 | 5 | ++ |
| | 10 | 5 | 5 | 5 | + |
| | 5 | 5 | 5 | 5 | — |
| 15 | 20 | 5 | 5 | 5 | ++ |
| | 10 | 5 | 5 | 5 | + |
| | 5 | 4 | 5 | 5 | — |
| 16 | 20 | 3 | 5 | 5 | + |
| | 10 | 2 | 5 | 4 | — |
| | 5 | 1 | 5 | 3 | — |
| 17 | 20 | 5 | 5 | 5 | ++ |
| | 10 | 5 | 5 | 5 | + |
| | 5 | 5 | 5 | 5 | — |
| 18 | 20 | 5 | 5 | 5 | ++ |
| | 10 | 5 | 5 | 5 | + |
| | 5 | 4 | 5 | 5 | — |
| 19 | 20 | 5 | 5 | 5 | +++ |
| | 10 | 5 | 5 | 5 | ++ |
| | 5 | 5 | 5 | 5 | + |
| 20 | 20 | 5 | 5 | 5 | ++ |
| | 10 | 5 | 5 | 5 | + |
| | 5 | 4 | 5 | 5 | — |
| 21 | 20 | 5 | 5 | 5 | +++ |
| | 10 | 5 | 5 | 5 | ++ |
| | 5 | 5 | 5 | 5 | + |
| 22 | 20 | 5 | 5 | 5 | ++ |
| | 10 | 5 | 5 | 5 | + |
| | 5 | 5 | 5 | 5 | — |
| 23 | 20 | 4 | 5 | 5 | + |
| | 10 | 3 | 5 | 5 | — |
| | 5 | 2 | 5 | 4 | — |
| 24 | 20 | 5 | 5 | 5 | ++ |
| | 10 | 5 | 5 | 5 | + |
| | 5 | 5 | 5 | 5 | — |
| 25 | 20 | 5 | 5 | 5 | + |
| | 10 | 4 | 5 | 5 | — |
| | 5 | 3 | 5 | 4 | — |
| 26 | 20 | 2 | 5 | 4 | — |
| | 10 | 1 | 5 | 3 | — |
| | 5 | 0 | 4 | 1 | — |
| | 20 | 5 | 5 | 5 | ++ |

TABLE 4-continued

Effects on Weeds in Paddy Fields

| Test Compound No. | Dose (g/a) | Echirochloa crus-gall | Monochoria vaginalis | Ammania multiflora | Phytotoxicity Rice |
|---|---|---|---|---|---|
| 27 | 10 | 5 | 5 | 5 | + |
|  | 5 | 4 | 5 | 5 | — |
|  | 20 | 5 | 5 | 5 | +++ |
| 28 | 10 | 5 | 5 | 5 | ++ |
|  | 5 | 4 | 5 | 4 | + |
|  | 20 | 2 | 5 | 5 | — |
| 29 | 10 | 1 | 4 | 2 | — |
|  | 5 | 0 | 3 | 1 | — |
|  | 20 | 5 | 5 | 5 | +++ |
| 30 | 10 | 5 | 5 | 5 | ++ |
|  | 5 | 5 | 5 | 5 | + |
|  | 20 | 2 | 5 | 5 | — |
| 31 | 10 | 1 | 5 | 4 | — |
|  | 5 | 0 | 4 | 3 | — |
|  | 20 | 2 | 5 | 4 | — |
| 32 | 10 | 1 | 4 | 3 | — |
|  | 5 | 0 | 3 | 2 | — |
|  | 20 | 5 | 5 | 5 | +++ |
| 33 | 10 | 5 | 5 | 5 | ++ |
|  | 5 | 4 | 5 | 5 | + |
|  | 20 | 5 | 5 | 5 | ++ |
| 34 | 10 | 5 | 5 | 5 | + |
|  | 5 | 4 | 5 | 5 | — |
|  | 20 | 2 | 5 | 4 | — |
| 35 | 10 | 1 | 4 | 3 | — |
|  | 5 | 0 | 2 | 1 | — |
| Reference MO | 20 | 5 | 5 | 5 | + |
|  | 10 | 4 | 5 | 5 | — |
|  | 5 | 3 | 4 | 4 | — |

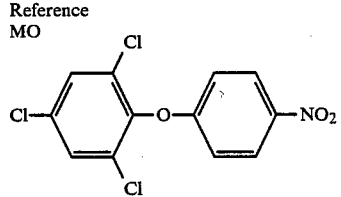

EXPERIMENT EXAMPLE 2 (EFFECT ON FIELD SOIL TREATMENT INFIELD)

The soil in a plowed field was filled in Wagner pots having an area of 1/5,000 are in which the seeds of *Digitaria adscendens, Chenopodium album* and *Amaranthus lividus* as weeds and of soybean as crop were sown and the seeds were covered with the soil of 1 cm in height. On the next day, the diluted solution of each of the waterdispersible powders described in Preparation Example 2 was uniformly dispersed on the covering soil. After 20 days from the treatment, the weed-killing effect and the phytotoxicity were examined in a way similar to that of Experimental Example 1. The results are shown in Table 5.

TABLE 5

Effects on Soil Treatment in Field

| Test Compound No. | Dose (g/a) | Digitaria adscendens | Chenopodium album | Amaranthus lividus | Phytotoxicity Soybean |
|---|---|---|---|---|---|
| 1 | 20 | 1 | 2 | 1 | — |
|  | 10 | 0 | 0 | 0 | — |
|  | 5 | 0 | 0 | 0 | — |
| 2 | 20 | 1 | 1 | 1 | — |
|  | 10 | 0 | 0 | 0 | — |
|  | 5 | 0 | 0 | 0 | — |
| 3 | 20 | 2 | 3 | 3 | — |
|  | 10 | 1 | 2 | 2 | — |
|  | 5 | 0 | 1 | 1 | — |
| 6 | 20 | 5 | 5 | 5 | + |
|  | 10 | 4 | 4 | 4 | — |
|  | 5 | 2 | 3 | 2 | — |
| 7 | 20 | 5 | 5 | 5 | + |
|  | 10 | 5 | 5 | 5 | — |
|  | 5 | 5 | 5 | 4 | — |
| 8 | 20 | 5 | 5 | 5 | + |
|  | 10 | 5 | 5 | 5 | — |
|  | 5 | 5 | 5 | 5 | — |
| 9 | 20 | 5 | 5 | 5 | — |
|  | 10 | 4 | 5 | 4 | — |
|  | 5 | 3 | 4 | 3 | — |
| 10 | 20 | 5 | 5 | 5 | + |
|  | 10 | 4 | 4 | 4 | — |

TABLE 5-continued

Effects on Soil Treatment in Field

| Test Compound No. | Dose (g/a) | Degree of Weed-Killing | | | Phytotoxicity Soybean |
|---|---|---|---|---|---|
| | | Digitaria adscendens | Chenopodium album | Amaranthus lividus | |
| 11 | 5 | 2 | 3 | 2 | — |
| | 20 | 5 | 5 | 4 | — |
| | 10 | 3 | 4 | 3 | — |
| 12 | 5 | 1 | 2 | 1 | — |
| | 20 | 5 | 5 | 5 | + |
| | 10 | 5 | 5 | 5 | — |
| 13 | 5 | 5 | 5 | 5 | — |
| | 20 | 4 | 5 | 5 | — |
| | 10 | 3 | 3 | 3 | — |
| 14 | 5 | 1 | 2 | 1 | — |
| | 20 | 5 | 5 | 5 | + |
| | 10 | 4 | 5 | 4 | + |
| 15 | 5 | 3 | 4 | 3 | — |
| | 20 | 5 | 5 | 5 | + |
| | 10 | 5 | 5 | 4 | — |
| 16 | 5 | 4 | 4 | 3 | — |
| | 20 | 2 | 4 | 3 | — |
| | 10 | 1 | 3 | 2 | — |
| 17 | 5 | 0 | 1 | 1 | — |
| | 20 | 5 | 5 | 5 | ++ |
| | 10 | 5 | 5 | 5 | + |
| 18 | 5 | 4 | 5 | 4 | — |
| | 20 | 5 | 5 | 5 | + |
| | 10 | 4 | 5 | 4 | — |
| 19 | 5 | 3 | 4 | 3 | — |
| | 20 | 5 | 5 | 5 | + |
| | 10 | 5 | 5 | 5 | — |
| 20 | 5 | 4 | 5 | 4 | — |
| | 20 | 3 | 4 | 5 | — |
| | 10 | 2 | 3 | 4 | — |
| 21 | 5 | 1 | 1 | 2 | — |
| | 20 | 5 | 5 | 5 | + |
| | 10 | 4 | 5 | 5 | — |
| 22 | 5 | 3 | 4 | 4 | — |
| | 20 | 4 | 5 | 5 | — |
| | 10 | 3 | 3 | 3 | — |
| 23 | 5 | 1 | 2 | 1 | — |
| | 20 | 3 | 4 | 4 | — |
| | 10 | 2 | 3 | 2 | — |
| 24 | 5 | 1 | 2 | 1 | — |
| | 20 | 5 | 5 | 5 | — |
| | 10 | 4 | 4 | 5 | — |
| 25 | 5 | 3 | 3 | 4 | — |
| | 20 | 2 | 5 | 4 | — |
| | 10 | 1 | 4 | 3 | — |
| 26 | 5 | 0 | 2 | 2 | — |
| | 20 | 2 | 3 | 3 | — |
| | 10 | 1 | 2 | 2 | — |
| 27 | 5 | 0 | 1 | 1 | — |
| | 20 | 5 | 4 | 5 | ++ |
| | 10 | 4 | 4 | 5 | + |
| 28 | 5 | 3 | 3 | 4 | + |
| | 20 | 5 | 5 | 5 | — |
| | 10 | 3 | 4 | 5 | — |
| 29 | 5 | 2 | 3 | 4 | — |
| | 20 | 2 | 2 | 3 | — |
| | 10 | 1 | 1 | 2 | — |
| 30 | 5 | 0 | 0 | 1 | — |
| | 20 | 5 | 5 | 5 | + |
| | 10 | 5 | 5 | 5 | — |
| 31 | 5 | 4 | 4 | 5 | — |
| | 20 | 1 | 2 | 3 | — |
| | 10 | 0 | 1 | 2 | — |
| 32 | 5 | 0 | 0 | 1 | — |
| | 20 | 2 | 2 | 3 | — |
| | 10 | 1 | 1 | 2 | — |
| 33 | 5 | 0 | 0 | 1 | — |
| | 20 | 5 | 5 | 5 | + |
| | 10 | 3 | 4 | 4 | — |
| 34 | 5 | 1 | 2 | 3 | — |
| | 20 | 5 | 5 | 5 | + |
| | 10 | 4 | 4 | 5 | — |
| 35 | 5 | 3 | 3 | 4 | — |
| | 20 | 1 | 1 | 2 | — |
| | 10 | 0 | 0 | 1 | — |
| | 5 | 0 | 0 | 0 | — |

TABLE 5-continued

| | | Effects on Soil Treatment in Field | | | |
| --- | --- | --- | --- | --- | --- |
| | | Degree of Weed-Killing | | | |
| Test Compound No. | Dose (g/a) | Digitaria adscendens | Chenopodium album | Amaranthus lividus | Phytotoxicity Soybean |
| Reference MO (2,4-dichloro-1-(4-nitrophenoxy)benzene structure) | 20 | 5 | 5 | 4 | + |
| | 10 | 5 | 4 | 3 | − |
| | 5 | 4 | 3 | 2 | − |

EXPERIMENT EXAMPLE 3 (EFFECT ON FOLIAGE TREATMENT)

The soil of a plowed field was filled in Wagner pots having an area of 1/5,000 are in which the seeds of weeds such as *Chenopodium album, Amaranthus lividus* and *Polygohum longisetum* were sown. After 20 days, the chemical solution of a given concentration which was obtained by diluting the emulsion prepared from each of the compounds to be examined in accordance with Preparation Example 1 with water was uniformly sprayed on the stalks and the leaves of the weeds grown so that the amount of water dispersed was 100 1/10a. After 20 days from the treatment, the weed-killing effect and the phytotoxicity (for corn) were evaluated in a way similar to that of Experimental Example 1. The results obtained are shown in Table 6.

TABLE 6

| | | Effects on Foliage Treatment | | | |
| --- | --- | --- | --- | --- | --- |
| | | Degree of Weed-Killing | | | |
| Test Compound No. | Dose (ppm) | Chenopodium album | Amaranthus lividus | Polygonum Longisetum | Phytotoxicity Corn |
| 1 | 2000 | 4 | 5 | 4 | + |
| | 1000 | 2 | 4 | 2 | − |
| | 500 | 1 | 2 | 1 | − |
| 2 | 2000 | 4 | 5 | 4 | + |
| | 1000 | 2 | 3 | 2 | − |
| | 500 | 1 | 2 | 1 | − |
| 3 | 2000 | 4 | 5 | 5 | + |
| | 1000 | 3 | 3 | 2 | − |
| | 500 | 2 | 2 | 1 | − |
| 6 | 2000 | 5 | 5 | 5 | ++ |
| | 1000 | 5 | 5 | 5 | + |
| | 500 | 5 | 4 | 4 | − |
| 7 | 2000 | 5 | 5 | 5 | ++ |
| | 1000 | 5 | 5 | 4 | + |
| | 500 | 5 | 4 | 3 | − |
| 8 | 2000 | 5 | 5 | 5 | + |
| | 1000 | 5 | 5 | 5 | − |
| | 500 | 5 | 4 | 4 | − |
| 9 | 2000 | 5 | 5 | 5 | + |
| | 1000 | 5 | 5 | 4 | − |
| | 500 | 4 | 3 | 3 | − |
| 10 | 2000 | 5 | 5 | 5 | + |
| | 1000 | 4 | 4 | 3 | − |
| | 500 | 3 | 2 | 2 | − |
| 11 | 2000 | 5 | 5 | 5 | + |
| | 1000 | 5 | 5 | 5 | − |
| | 500 | 3 | 4 | 3 | − |
| 12 | 2000 | 5 | 5 | 5 | +++ |
| | 1000 | 5 | 5 | 5 | ++ |
| | 500 | 5 | 5 | 5 | + |
| 13 | 2000 | 5 | 5 | 5 | ++ |
| | 1000 | 4 | 4 | 4 | + |
| | 500 | 3 | 2 | 2 | − |
| 14 | 2000 | 5 | 5 | 5 | ++ |
| | 1000 | 5 | 4 | 4 | + |
| | 500 | 4 | 4 | 3 | − |
| 15 | 2000 | 5 | 5 | 5 | + |
| | 1000 | 5 | 5 | 5 | − |
| | 500 | 5 | 4 | 5 | − |
| 16 | 2000 | 4 | 5 | 5 | + |
| | 1000 | 3 | 4 | 3 | − |
| | 500 | 2 | 3 | 1 | − |
| 17 | 2000 | 5 | 5 | 5 | ++ |
| | 1000 | 5 | 5 | 5 | + |
| | 500 | 5 | 4 | 4 | − |
| 18 | 2000 | 5 | 5 | 5 | ++ |
| | 1000 | 5 | 4 | 5 | + |
| | 500 | 5 | 3 | 5 | − |

TABLE 6-continued

Effects on Foliage Treatment

| Test Compound No. | Dose (ppm) | Degree of Weed-Killing | | | Phytotoxicity Corn |
|---|---|---|---|---|---|
| | | Chenopodium album | Amaranthus lividus | Polygonum Longisetum | |
| 19 | 2000 | 5 | 5 | 5 | ++ |
| | 1000 | 5 | 5 | 5 | + |
| | 500 | 5 | 4 | 4 | — |
| 20 | 2000 | 5 | 5 | 5 | + . |
| | 1000 | 5 | 5 | 4 | — |
| | 500 | 4 | 4 | 3 | — |
| 21 | 2000 | 5 | 5 | 5 | ++ |
| | 1000 | 5 | 5 | 5 | + |
| | 500 | 5 | 4 | 4 | — |
| 22 | 2000 | 5 | 5 | 5 | ++ |
| | 1000 | 5 | 5 | 4 | + |
| | 500 | 4 | 4 | 3 | — |
| 23 | 2000 | 5 | 5 | 5 | +++ |
| | 1000 | 5 | 5 | 5 | + |
| | 500 | 2 | 3 | 4 | — |
| 24 | 2000 | 5 | 5 | 5 | ++ |
| | 1000 | 4 | 5 | 5 | + |
| | 500 | 2 | 3 | 4 | — |
| 25 | 2000 | 5 | 5 | 5 | ++ |
| | 1000 | 4 | 5 | 5 | — |
| | 500 | 3 | 4 | 5 | — |
| 26 | 2000 | 4 | 5 | 5 | — |
| | 1000 | 2 | 3 | 4 | — |
| | 500 | 1 | 2 | 3 | — |
| 27 | 2000 | 5 | 5 | 5 | + |
| | 1000 | 4 | 5 | 5 | — |
| | 500 | 3 | 3 | 4 | — |
| 28 | 2000 | 5 | 5 | 5 | + |
| | 1000 | 5 | 5 | 5 | — |
| | 500 | 4 | 4 | 5 | — |
| 29 | 2000 | 3 | 5 | 5 | — |
| | 1000 | 2 | 3 | 4 | — |
| | 500 | 1 | 2 | 3 | — |
| 30 | 2000 | 5 | 5 | 5 | ++ |
| | 1000 | 5 | 5 | 5 | + |
| | 500 | 4 | 5 | 5 | — |
| 31 | 2000 | 5 | 5 | 4 | — |
| | 1000 | 4 | 4 | 3 | — |
| | 500 | 3 | 2 | 1 | — |
| 32 | 2000 | 2 | 3 | 3 | — |
| | 1000 | 1 | 2 | 2 | — |
| | 500 | 0 | 1 | 0 | — |
| 33 | 2000 | 5 | 5 | 5 | + |
| | 1000 | 4 | 5 | 4 | — |
| | 500 | 2 | 4 | 3 | — |
| 34 | 2000 | 5 | 5 | 5 | + |
| | 1000 | 4 | 5 | 5 | + |
| | 500 | 3 | 4 | 4 | — |
| 35 | 2000 | 4 | 5 | 5 | + |
| | 1000 | 3 | 4 | 2 | — |
| | 500 | 2 | 2 | 1 | — |
| Reference MO | 2000 | 5 | 5 | 5 | ++ |
| | 1000 | 5 | 4 | 5 | + |
| | 500 | 4. | 3 | 3 | — |

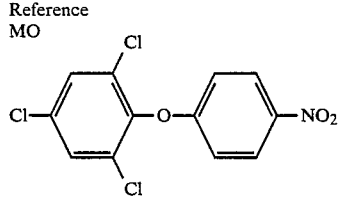

We claim:

1. A hydantoin derivative represented by the formula:

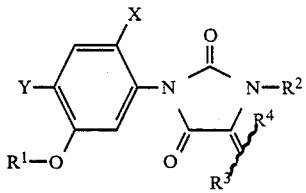

wherein X and Y are independently halogen atoms, $R^1$ represents a hydrogen atom, a $C_3$–$C_4$ alkenyl group or a $C_3$–$C_4$ alkynyl group, $R^2$ represents a hydrogen atom, a methyl group or an ethyl group, and $R^3$ and $R^4$ independently represent a hydrogen atom or a $C_1$–$C_3$ alkyl group.

2. A hydantoin derivative according to claim 1, wherein X is a chlorine atom or a fluorine atom, Y is a chlorine atom or a bromine atom, $R^1$ is a propargyl group, and $R^3$ and $R^4$ are both methyl groups.

3. A herbicidal composition comprising an agriculturally acceptable carrier an a herbicidally effective amount of a hydantoin derivative represented by the formula:

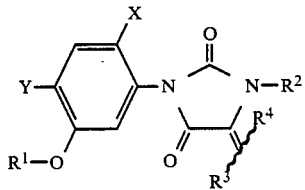

wherein x and Y are independently halogen atoms, $R^1$ represents a hydrogen atom, a $C_3$–$C_4$ alkenyl group or a $C_3$–$C_4$ alkynyl group, $R^2$ represents a hydrogen atom, a methyl group or an ethyl group, and $R^3$ and $R^4$ independently represent a hydrogen atom or a $C_1$–$C_3$ alkyl group.

4. A herbicidal composition according to claim 3, wherein X is a chlorine atom or a fluorine atom, Y is a chlorine atom or a bromine atom, $R^1$ is a propargyl group, and $R^3$ and $R^4$ are both methyl groups.

* * * * *